US007376677B2

(12) United States Patent
Ober et al.

(10) Patent No.: US 7,376,677 B2
(45) Date of Patent: *May 20, 2008

(54) SYSTEM AND METHOD FOR GENERATING DE-IDENTIFIED HEALTH CARE DATA

(75) Inventors: N. Stephen Ober, Southboro, MA (US); John Grubmuller, Bedford, NH (US); Maureen Farrell, Bedford, MA (US); Charles Wentworth, Attleboro, MA (US); Tom Gilbert, Holliston, MA (US); Kevin Barrett, Sherborn, MA (US); Steven Davis, Brookline, MA (US); Erik Nordman, Waltham, MA (US); Randell Grenier, Waltham, MA (US)

(73) Assignee: Verispan, L.L.C., Yardley, PA (US)

( * ) Notice: Subject to any disclaimer, the term of this patent is extended or adjusted under 35 U.S.C. 154(b) by 536 days.

This patent is subject to a terminal disclaimer.

(21) Appl. No.: 10/801,086

(22) Filed: Mar. 15, 2004

(65) Prior Publication Data
US 2005/0114334 A1 May 26, 2005

Related U.S. Application Data

(63) Continuation of application No. 09/665,420, filed on Sep. 20, 2000, now Pat. No. 6,732,113.

(60) Provisional application No. 60/154,726, filed on Sep. 20, 1999.

(51) Int. Cl.
*G06F 17/30* (2006.01)
*G06F 15/16* (2006.01)

(52) U.S. Cl. .................... 707/204; 707/100; 707/200; 709/205; 709/217

(58) Field of Classification Search ............. None
See application file for complete search history.

(56) References Cited

U.S. PATENT DOCUMENTS 3,752,904 A  8/1973  Waterbury (Continued)

OTHER PUBLICATIONS

Chaudhuri Set al: "An Overview of Data Warehousing and OLAP Technology" Sigmod Record, Sigmod, New York, NY, US, vol. 26, No. 1, Mar. 1997, pp. 65-74, XP002193792, ISSN: 0163-5808.

(Continued)

*Primary Examiner*—Tony Mahmoudi
(74) *Attorney, Agent, or Firm*—Needle & Rosenberg, P.C.

(57) ABSTRACT

A system and method for creating a unique alias associated with an individual identified in a health care database such that health care data, and particularly pharmaceutical-related data, can be efficiently gathered and analyzed. The system has a first data store for storing at least one record where each record includes a plurality of identification fields which when concatenated uniquely identify an individual, and at least one health care field corresponding to health care data associated with the individual. The system also has a second data store, and a processor. The processor selects a record of the first data store, then selects a subset of the plurality of identification fields within the selected record, and concatenates the selected subset of identification fields. Then the processor stores the concatenated identification fields in a record in the second data store with the at least one health care field from the selected record of the first data store.

20 Claims, 17 Drawing Sheets

U.S. PATENT DOCUMENTS

| | | | |
|---|---|---|---|
| 3,896,266 A | 7/1975 | Waterbury | |
| 4,993,068 A | 2/1991 | Piosenka et al. | |
| 5,003,539 A | 3/1991 | Takemoto et al. | |
| 5,005,200 A | 4/1991 | Fischer | |
| 5,070,452 A | 12/1991 | Doyle, Jr. et al. | |
| 5,214,702 A | 5/1993 | Fischer | |
| 5,299,121 A | 3/1994 | Brill et al. | |
| 5,301,105 A | 4/1994 | Cummings, Jr. | |
| 5,371,797 A | 12/1994 | Bocinsky, Jr. | |
| 5,471,382 A | 11/1995 | Tallman et al. | |
| 5,502,764 A | 3/1996 | Naccache | |
| 5,644,778 A | 7/1997 | Burks et al. | |
| 5,652,842 A | 7/1997 | Siegrist, Jr. et al. | |
| 5,664,109 A | 9/1997 | Johnson et al. | |
| 5,666,492 A * | 9/1997 | Rhodes et al. | 705/3 |
| 5,704,044 A | 12/1997 | Tarter et al. | |
| 5,724,575 A * | 3/1998 | Hoover et al. | 707/10 |
| 5,754,938 A | 5/1998 | Herz et al. | |
| 5,758,085 A | 5/1998 | Kouoheris et al. | |
| 5,758,095 A | 5/1998 | Albaum et al. | |
| 5,787,186 A | 7/1998 | Schroeder | |
| 5,793,969 A | 8/1998 | Kamentsky et al. | |
| 5,799,086 A | 8/1998 | Sudia | |
| 5,799,308 A | 8/1998 | Dixon | |
| 5,821,871 A | 10/1998 | Benzler | |
| 5,825,906 A | 10/1998 | Obata et al. | |
| 5,832,449 A | 11/1998 | Cunningham | |
| 5,867,821 A | 2/1999 | Ballantyne et al. | |
| 5,876,926 A | 3/1999 | Beecham | |
| 5,890,129 A | 3/1999 | Spurgeon | |
| 5,915,240 A | 6/1999 | Karpf | |
| 5,918,208 A | 6/1999 | Javitt | |
| 5,920,854 A | 7/1999 | Kirsch et al. | |
| 5,956,716 A | 9/1999 | Kenner et al. | |
| 5,970,462 A | 10/1999 | Reichert | |
| 5,991,731 A | 11/1999 | Colon et al. | |
| 5,995,939 A | 11/1999 | Berman et al. | |
| 6,003,006 A | 12/1999 | Colella et al. | |
| 6,012,051 A | 1/2000 | Sammon, Jr. et al. | |
| 6,014,631 A | 1/2000 | Teagarden et al. | |
| 6,018,713 A | 1/2000 | Coli et al. | |
| 6,024,287 A | 2/2000 | Takai et al. | |
| 6,079,021 A | 6/2000 | Abadi et al. | |
| 6,249,768 B1 * | 6/2001 | Tulskie et al. | 705/7 |
| 6,266,675 B1 | 7/2001 | Evans et al. | 707/104 |
| 6,302,844 B1 | 10/2001 | Walker et al. | 600/300 |
| 6,341,267 B1 * | 1/2002 | Taub | 705/11 |
| 6,421,650 B1 | 7/2002 | Goetz et al. | 705/3 |
| 6,496,931 B1 * | 12/2002 | Rajchel et al. | 713/168 |
| 6,732,113 B1 * | 5/2004 | Ober et al. | 707/102 |

OTHER PUBLICATIONS

Brannigan V M and Beier B R: "Patient privacy in the era of medical computer networks: a new paradigm for a new technology." Proceedings of the Eighth World Congress on Medical Informatics, vol. 8, No. 1, Jul. 23, 1995-Jul. 27, 1995 pp. 640-643, XP009040274, Vancouver, British Columbia, Canada, ISSN: 1569-6332.

Quantin C et al: "How to ensure data security of an epidemiological follow-up: quality assessment of an anonymous record linkage procedure" International Journal of Medical Informatics, Elsevier Scientific Publishers, Shannon, IR, vol. 49, No. 1, Mar. 1998, pp. 117-122, XP004149470, ISSN: 1386-5056.

Anderson R J: "A security policy model for clinical information systems" Security and Privacy, 1996. Proceedings., 1996 IEEE Symposium on Oakland, CA, USA May 6-8, 1996, Los Alamitos, CA, USA,IEEE Comput. Soc, US, May 6, 1996, pp. 30-43, XP01064923, ISBN: 0-8186-7417-2.

Supplementary European Search Report of EP 00 96 5216.
International Search Report of PCT/US00/25818.

* cited by examiner

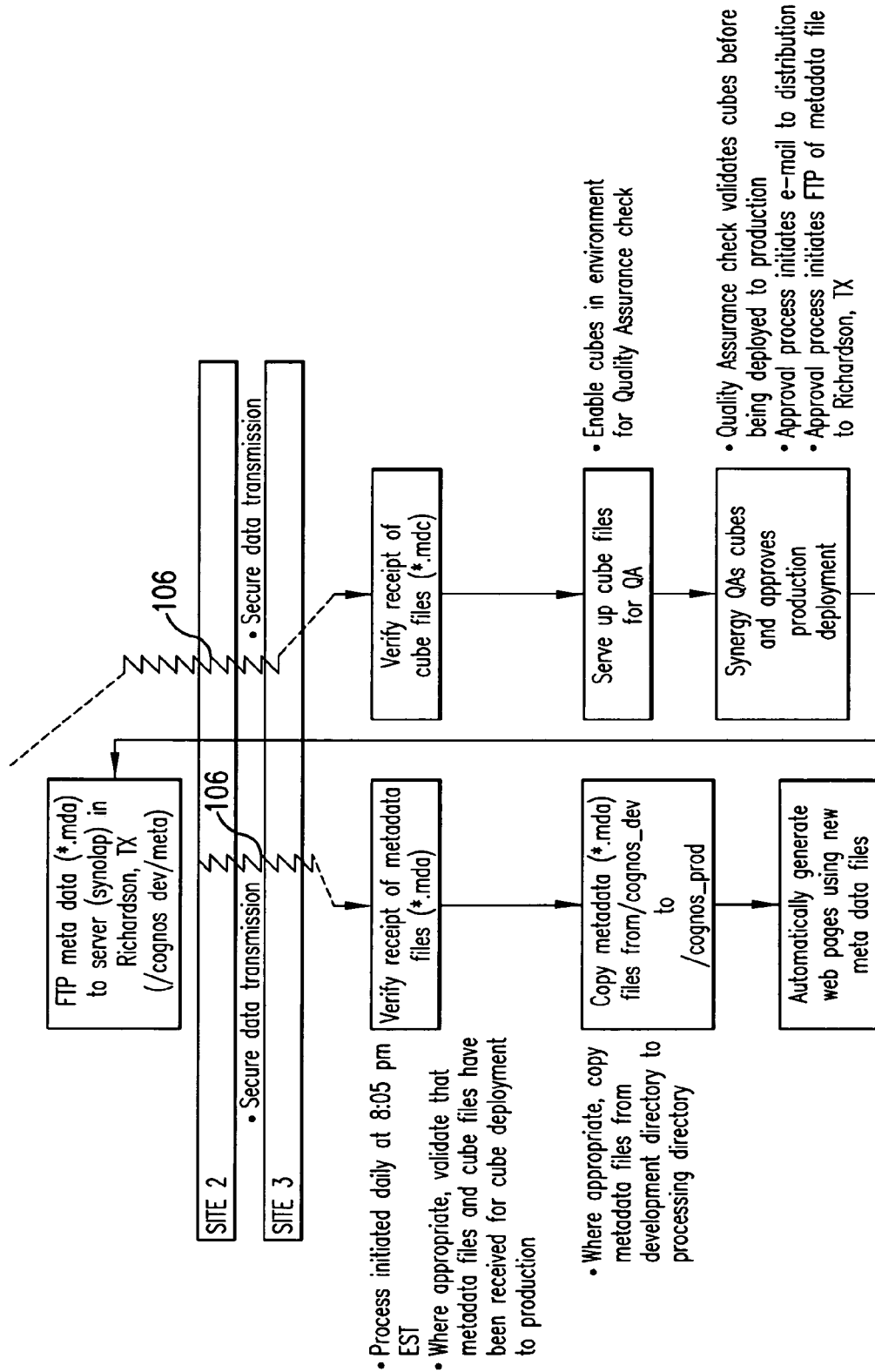

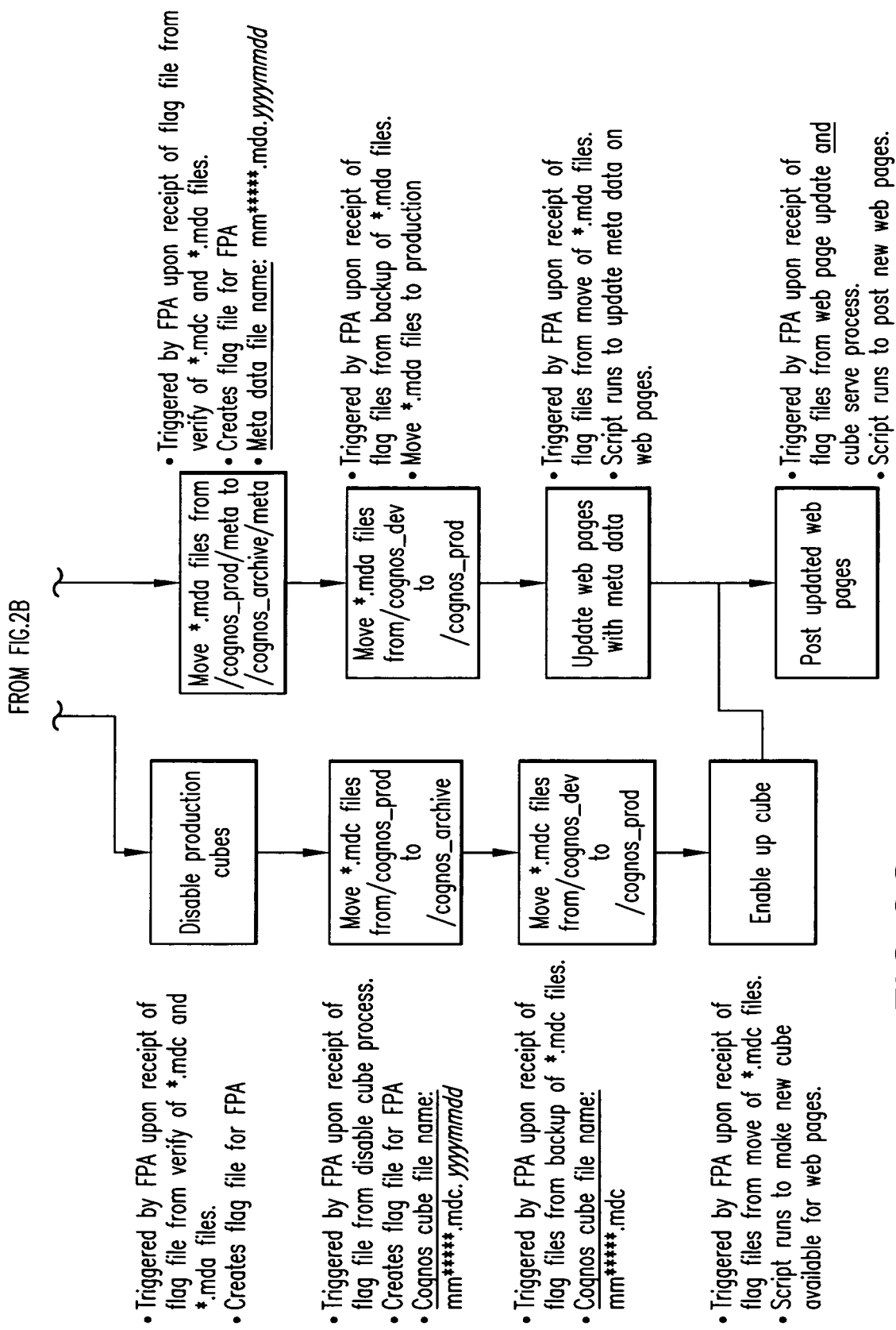

SYSTEM AND METHOD FOR GENERATING DE-IDENTIFIED HEALTH CARE DATA

CROSS-REFERENCE TO RELATED APPLICATION

The present application is a continuation application from, and claims the benefit of and priority to, pursuant to U.S.C. § 119(e), application Ser. No. 09/665,420, filed Sep. 20, 2000, now U.S. Pat. No. 6,732,113 which claims priority to U.S. Provisional Application No. 60/154,726, filed Sep. 20, 1999, which applications are hereby incorporated by reference herein in their entirety.

BACKGROUND OF THE INVENTION

1. Field of the Invention

The present invention generally relates to computer systems and databases. More particularly, the present invention relates to a system and method for the gathering and analysis of health-care related data, and specifically the gathering and analysis of information regarding the use of pharmaceuticals by individuals. The present invention also relates to techniques for de-identifying the individuals from such pharmaceutical data, in order to maintain privacy.

2. Description of the Related Art

In the medical information field, pharmaceutical claims are processed on large computer systems which receive claims data for patients who have been prescribed one or more medications and have filed claims with insurance companies (or government entities) in order to have the claim paid by the company or entity. The claims data includes very specific details and attributes about the individuals making the claims. For example, attributes can include name, gender, birth date, address, medical diagnosis, specific drug prescribed, and other drugs the patient is using. Consequently, this data is very useful in assisting marketing research relative to usage of a specific drug and identifying various attributes that impact the usage.

The claims data is typically received at a data "clearing-house" which can be a database for a specific insurance company or a larger database providing the claim processing service for many insurance companies. Moreover, the claims data that are produced by claimants include a significant amount of data, with millions of new claims being entered into the system each month. Several of the claims data clearinghouses have systems handling many terabytes of claims data. Because of the large size of the data being produced and the large amount of attributes, the data is in an inadequate format for efficient search, retrieval and analysis of specific attributes.

Recently, there have been laws passed that prevent the transmission of personal information associated with individuals, within health care claims data. This legislation particularly prohibits the transfer of specific personal data such as names, addresses and social security numbers. Thus, the claims data is no longer allowed to be transmitted from the clearinghouse to others in raw form with the personal data. Without the personal information to segregate the claims data, it becomes much harder to generate valuable research and market data based upon the unique attributes for specific individuals, such as age, gender and geographic distribution.

It is therefore desirous to provide the ability to efficiently gather information from the claims databases to allow research and analysis of the attributes that effect the pharmaceutical industry. Accordingly, the present invention is primarily directed to systems and methods for overcoming the problems discussed above, as well as related limitations of the prior art.

SUMMARY OF THE INVENTION

In one embodiment, the present invention is directed to a system and method for creating a unique alias associated with an individual identified in a health care database, that allows the aggregation of segregated data for marketing research. The system may include a first data store for storing at least one record where each record has a plurality of identification fields, such as name and birth date, which when concatenated uniquely identify an individual, and at least one health care field corresponding to health care data associated with the individual, such as a medication type. The system may also have a second data store and a processor that selects a record of the first data store, selects a subset of the plurality of identification fields within the selected record, concatenates the selected subset of identification fields, and stores the concatenated identification fields in a record in the second data store along with at least one health care field from the selected record of the first data store. The first data store and the second data store can either be located within the same database or in separate databases.

The health care data stored within the first data store may, in one embodiment, correspond to pharmaceutical claims data. The selected subset may correspond to a specific person in the healthcare database, and the person's last name, birthday, and gender are concatenated to form a unique identifier for that record. The processor may analyze longitudinal and historical records of individuals using individual-level linking methodologies based on the concatenated identification fields and the at least one health care field of each record of the second data store. The health care data also can have personal data removed from the various records such that only medically significant information remains, and the identifier allows the medical information to be segregated such that the individual records are still identifiable.

In order to more efficiently process the tremendous amount of data of the health care records, the processor may perform the further steps of selectively gathering the records from the first data store and selectively manipulating the records into a data cube. The records of the first data store are typically in tabular form, and the process of manipulating the records comprises selectively joining and projecting records from the various tabular records in the first data store to ultimately form a data cube comprised of a table of records. The data cube format allows the processor to more easily perform a search of the health care records, and also generate a report by displaying the records of a specific data cube.

The present invention thus provides a method for creating a unique alias associated with an individual identified in a health care database, wherein the health care database stores at least one record, and each record has a plurality of identification fields which when taken together uniquely identify an individual, and at least one health care field may correspond to health care data associated with the individual. The method includes the steps of selecting a record within the health care database, selecting a subset of the plurality of identification fields within the selected record, concatenating the selected subset of identification fields, and storing the concatenated identification fields in a record in a second database with the at least one health care field from the selected record of the first data store. The method preferably includes the step of analyzing longitudinal, historical records of individuals using individual-level linking methodologies based on the concatenated identification fields and the at least one health care field of each record of the second database.

The step of selecting a record within the health care database may comprise selecting a record from pharmaceutical claims data. Further, the step of concatenating the selected subset of identification fields may comprise, for example, concatenating, for a specific person in the healthcare database, that person's last name, birthday, and gender. Thus, based on the concatenated identification fields and the at least one health care field of each record of the second data store, the method may include the step of analyzing longitudinal, historical records of individuals using individual-level linking methodologies.

As discussed above, the method further may include the steps of selectively gathering the records from the first data store, and selectively manipulating the records into a data cube. The step of selecting a record within the health care database may comprise selecting records of the first data store that are in tabular form, and the step of selectively manipulating the records into a data cube may comprise selectively joining and projecting records from the first data store and creating a data cube comprising a table of records.

The data cube allows the present system to aggregate the records in an efficient format such that all new records can be viewed shortly after posting. Further, the unique population identifiers allow users to follow patients over time yielding important results unavailable in other databases, such as patient drug switching behavior. By linking medical and pharmacy transactions at the patient level, new insights such as indication specific use of drugs and patient comorbidities can be determined.

The report displayed by the system may contain several attributes, such as: market shares geographic information at the national, regional, state and MSA levels; trends over time including annual, quarterly, monthly, and weekly periods; traditional measures such as total, new and refilled prescription counts; source of business such as new prescription starts, switches, and continuing patients; prescriber specialty; patient demographics for age and gender; indication specific use; and patient comorbidities. The system can therefore be used in a number of ways to help make business decisions, such as monitoring new drug launches and marketing campaigns, enhanced sales force targeting, and micro-marketing in select geographic areas or to select customers. Furthermore, the system can be used for forecasting and development of a pharmaceutical marketing strategy including indication-specific product positioning, early warning market share shifts, clinical trial site selection, investigator recruiting, and accurate intelligence on market size and demand.

Other objects, features, and advantages of the present invention will become apparent from the drawings, detailed description of the invention, and the claims, below.

DETAILED DESCRIPTION OF THE INVENTION

Figures 1, 1A:
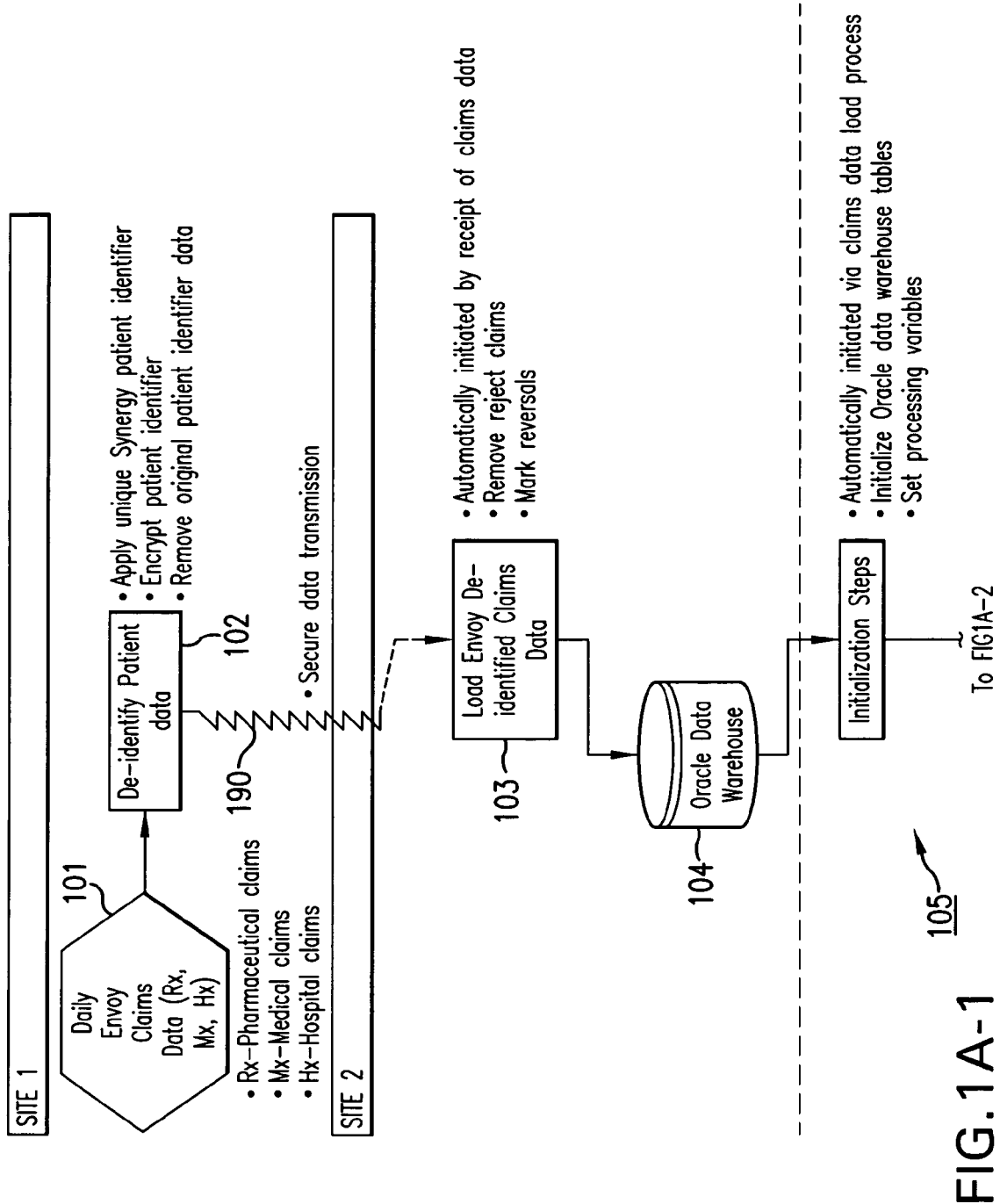
FIGS. 1A, 1B, 1C and 2 are block and flow diagrams showing the overall structure and overall flow of the present invention in one embodiment.
Figures 1, 1A, 2:
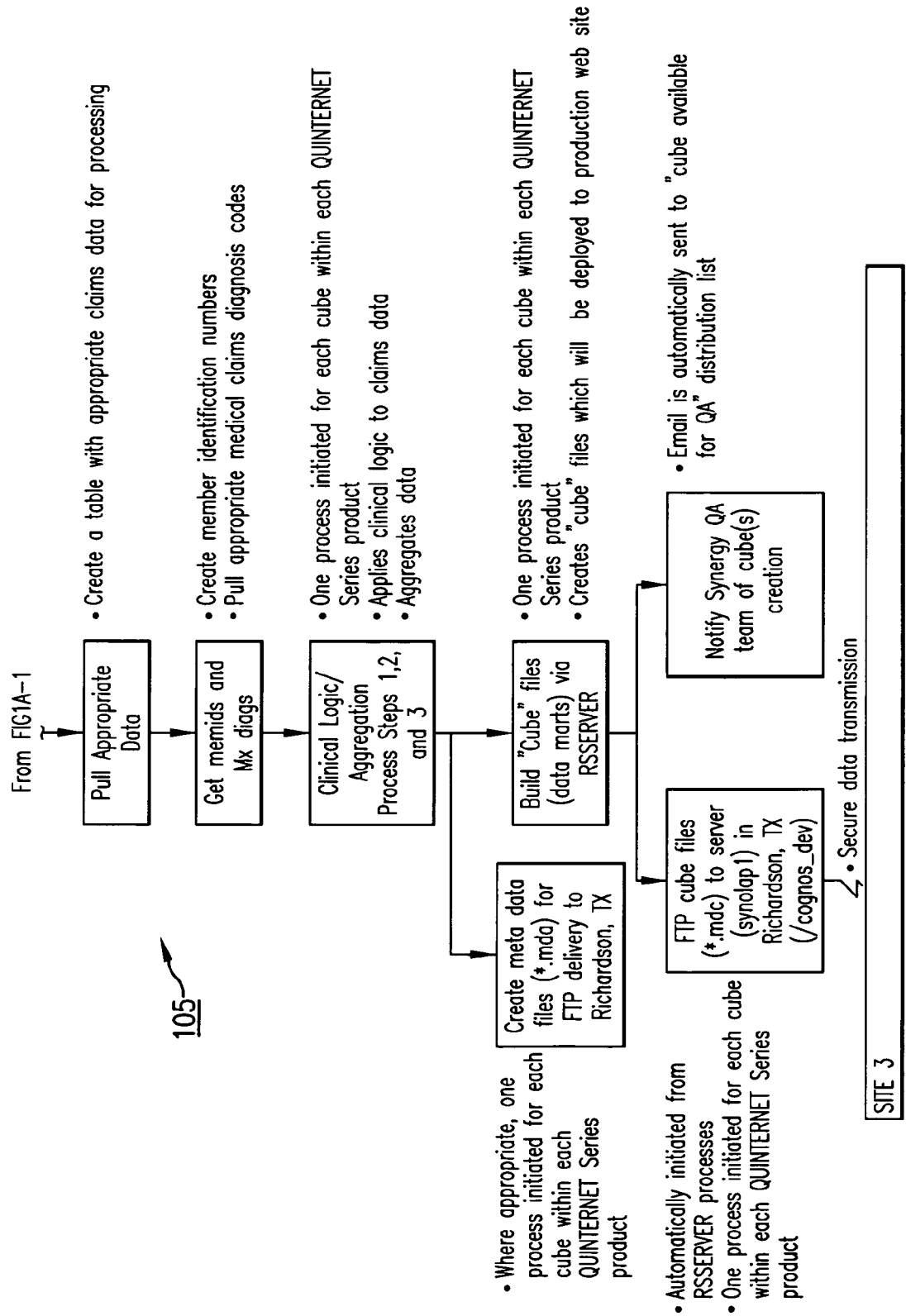
Figures 1, 1B, 2:
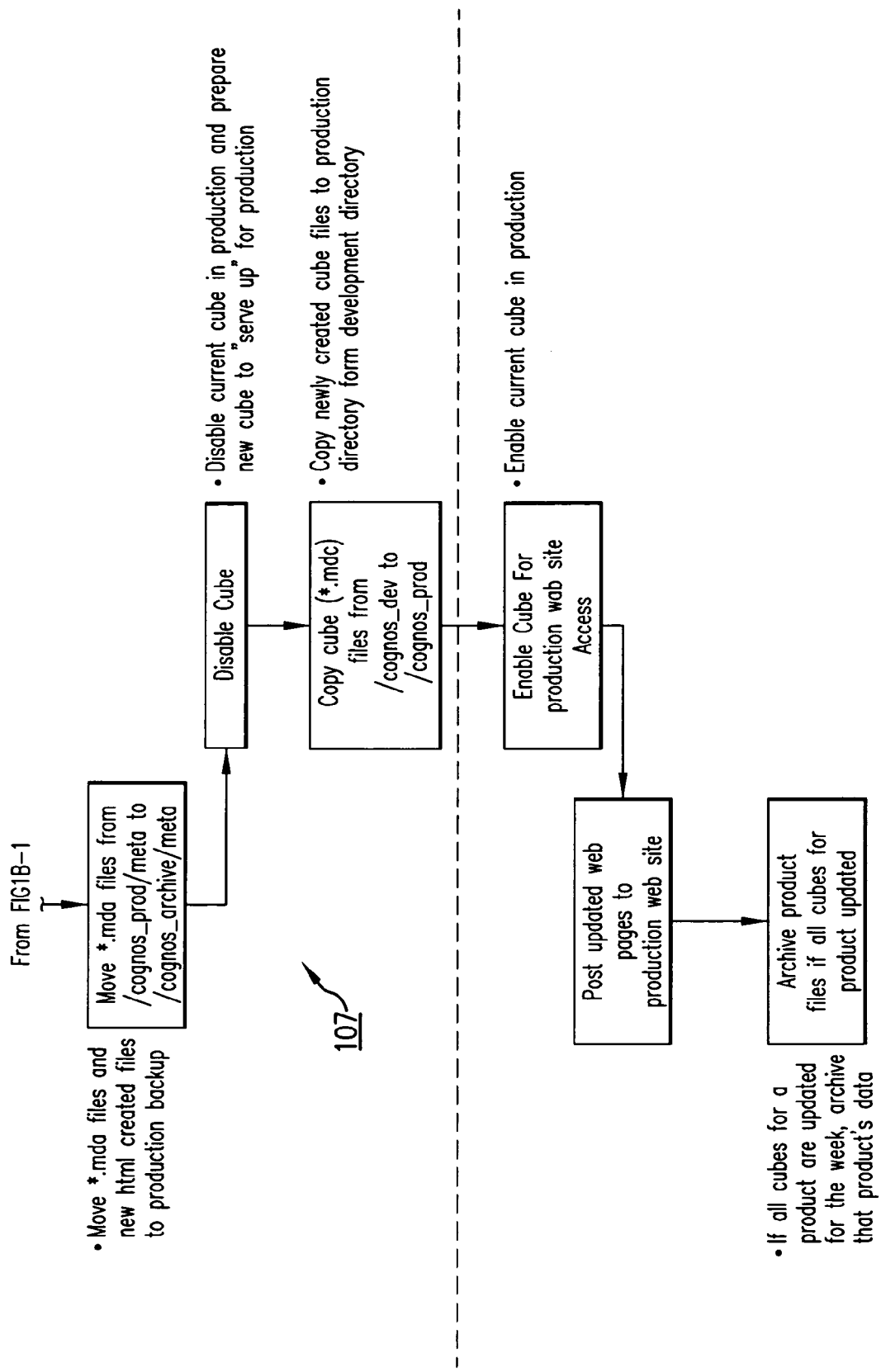

With reference to the drawings, in which like numerals represent like elements throughout, FIGS. 1A, 1B and 2 illustrate a high-level combined block/flow diagram for the present invention. These figures represent both the elements of a block diagram for, as well as the steps performed by the system of, the present invention.

Referring to FIGS. 1A, 1B and 2, the primary processing that takes place in the present invention may be performed by, for example, a high-performance computing system, such as a Sun Microsystems ES 10000 computer (at SITE 2). On a periodic basis, such as each day, seven days per week, a computing system at SITE 1 places healthcare claims data at step 103 via a secure connection 190 onto a computer system at SITE 1. This healthcare claims data may include, for example, pharmaceutical, medical, and hospital claims 101 that have been "de-identified" at step 102 (explained in further detail below).

The claims data is de-identified at step 102 before it is sent to SITE 2, which includes applying a unique identifier, encrypting this identifier, and removing specific patient identifying fields. Data is then loaded into database tables (such as an Oracle database) at step 104 that also reside on SITE 2. At step 105, SITE 2 runs all processes for analyzing and consolidating the data and for transforming the resulting Oracle tables into OLAP cubes.

The cube building process may run on a different computer (such as SITE 2). Cubes are modeled using an OLAP product on a desktop computer under, for example, the Windows NT operating system.

The cube deployment process may run on a different computer (such as SITE 3). A computing system at SITE 2 places cubes and metadata files at step 106 via a secure connection to SITE 3. Processes run at step 107 at SITE 3 to place the cube on the production web site and to update the web site pages with the associated metadata.

Figure 3A:
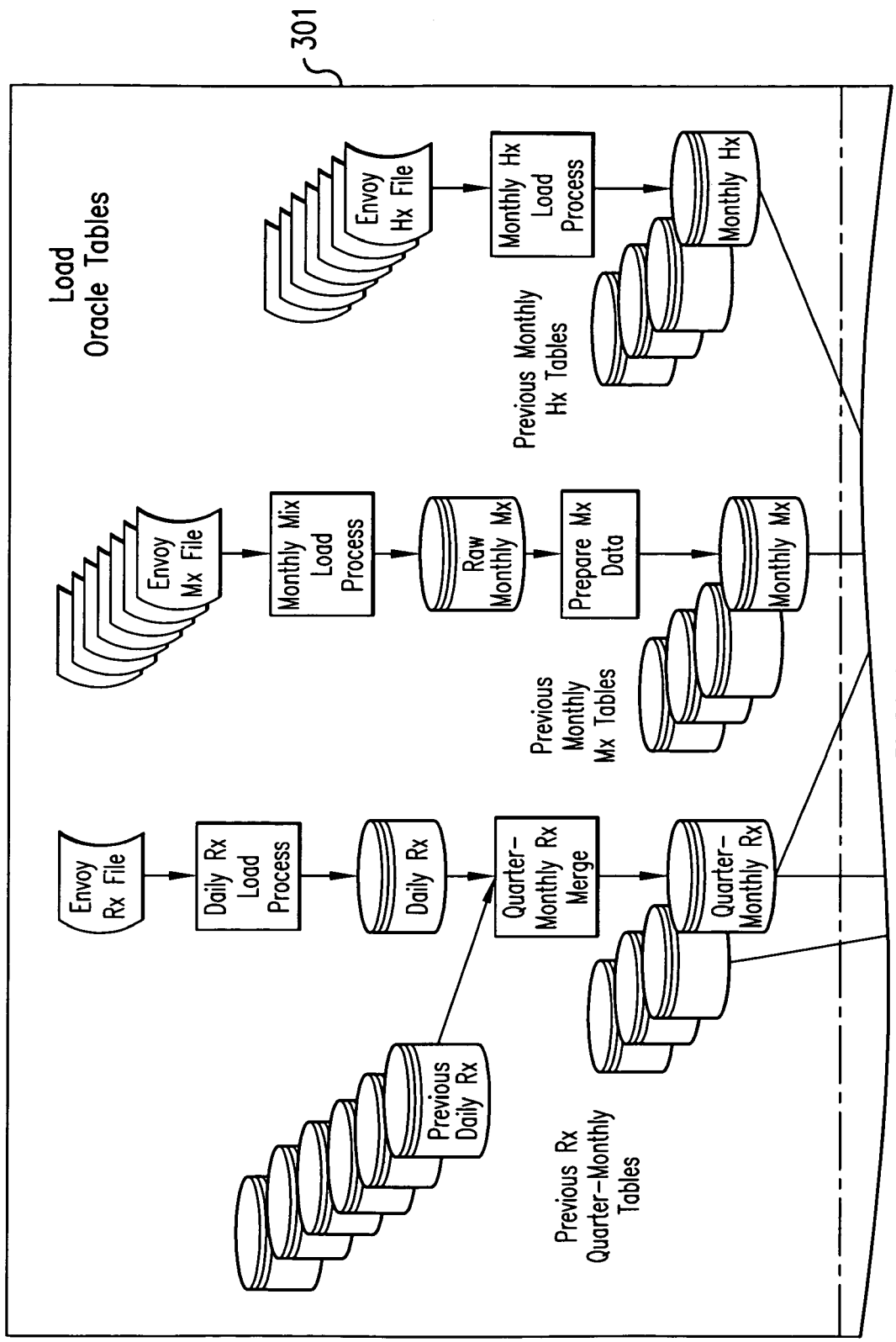
FIG. 3 is a flow and relationship diagram, showing the overall flow and data relationship of the present invention.
Figure 3B:
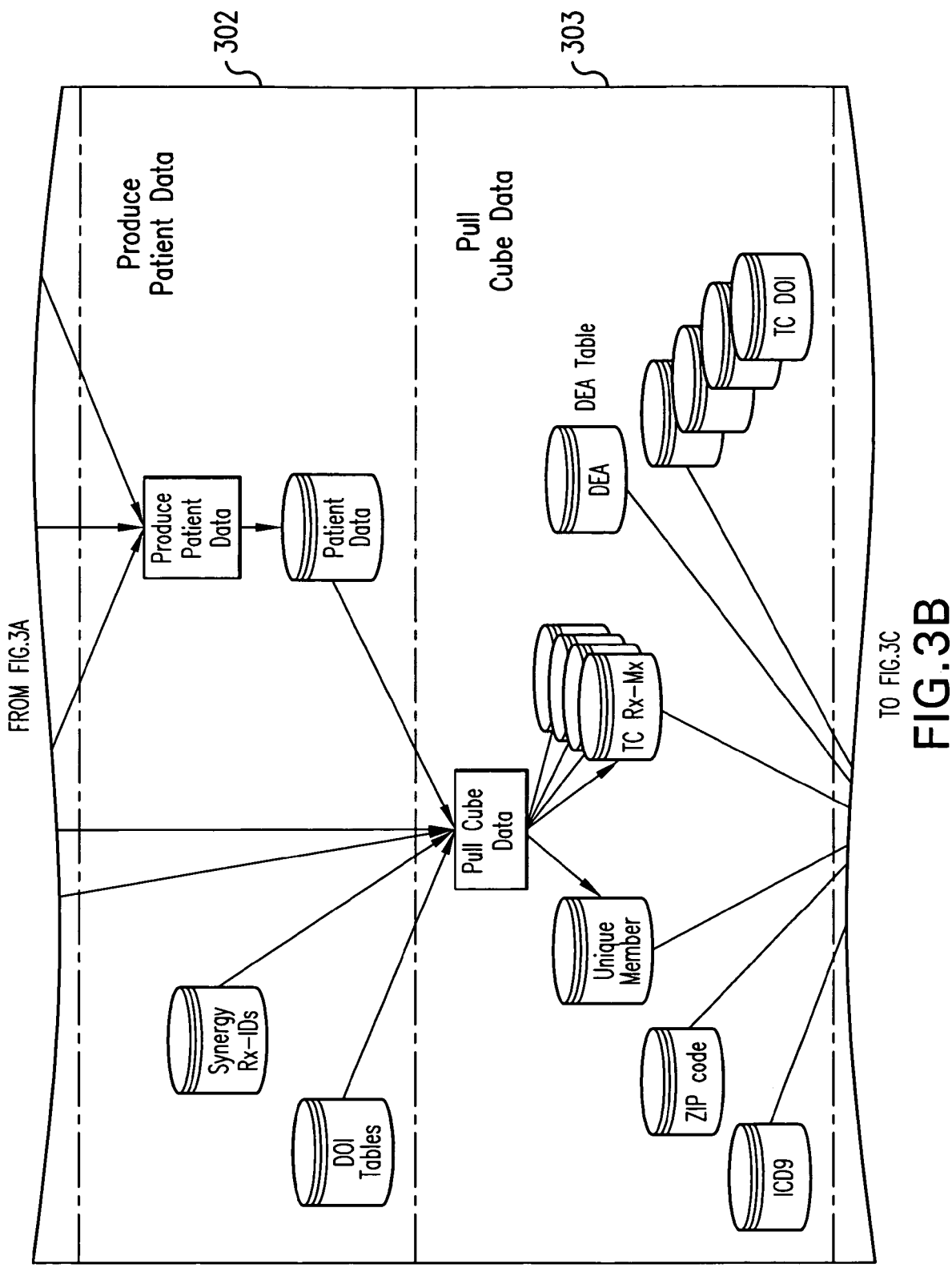
Figure 3C:
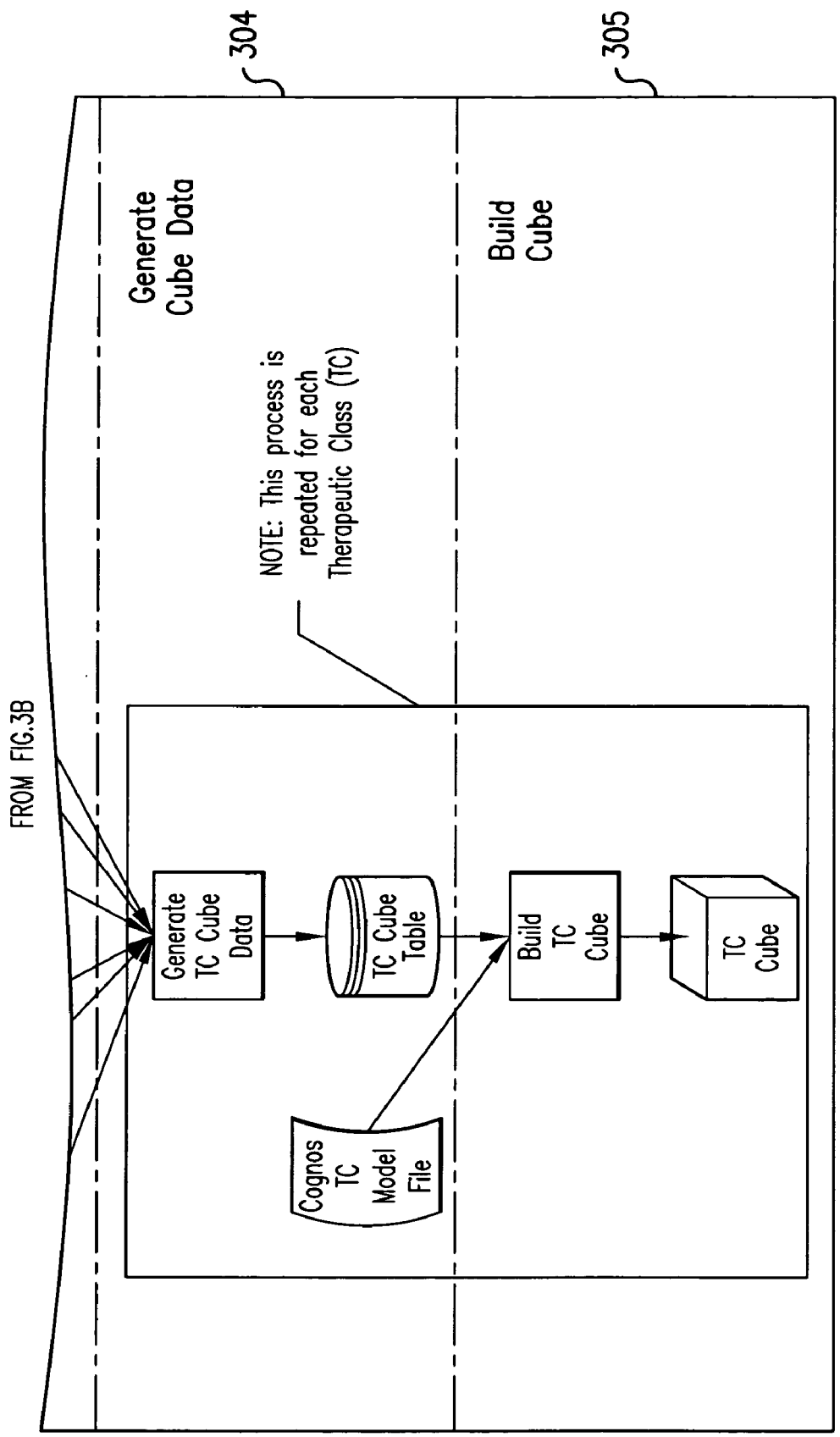

The present process performed at SITE 2 after obtaining data from the SITE 1 computer, making data ready for cube transformers, and then displaying it on the web at SITE 3 can be logically divided into six major steps, as shown in FIG. 3.

1. Load Oracle Tables (step 301)
2. Produce Patient Data (step 302)
3. Pull Cube Data (step 303)
4. Generate Cube Data (step 304)
5. Build Cube (step 305)
6. Automated Cube Deployment and Metadata Update Process All these processes are handled, maintained and executed at regular daily, weekly and monthly intervals. There are some processes which are done out of the routine process, such as generation of DOI, zip-state-region, ICD9, etc. tables. FIG. 3 shows a high level overview of the processes used to create cubes.

1. Load Oracle Tables (Step 301)

The Load Oracle Tables process (step 301) can be divided into two logically different steps, daily and monthly processes, described in further detail below with respect to FIGS. 4-8. The daily routines convert the text format data supplied from SITE 1 into "RX" and "Do Not Use Company Name (DNU)" daily Oracle tables. The monthly processes convert Hospital (HX) and Medical (MX) data into monthly Oracle tables. Note that all run times provided below correspond to approximate run times.

1.1 Daily Rx Load Process 401

Figure 4:
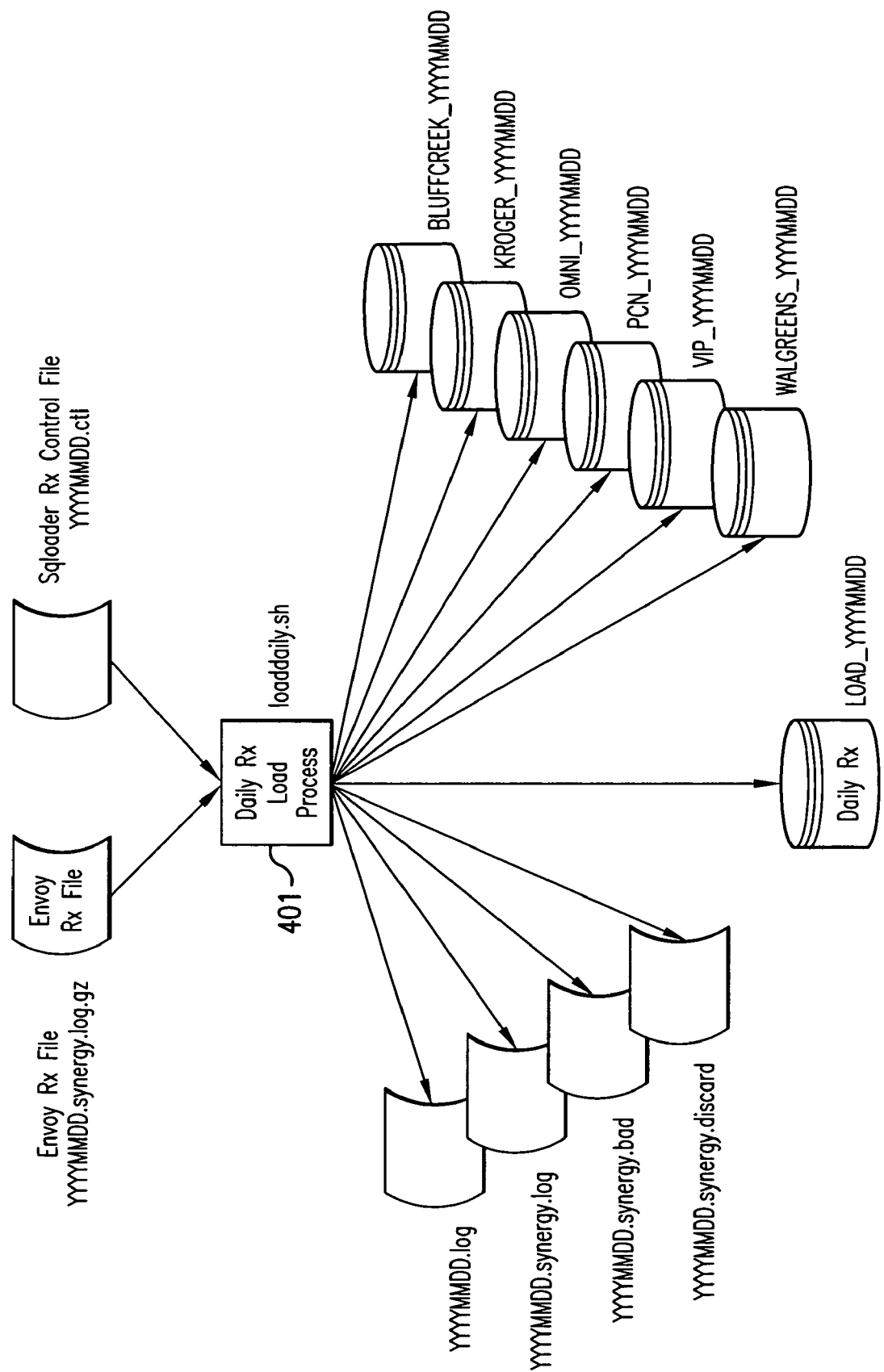
FIG. 4 illustrates the operation of the Daily Rx Load Process of the present invention.

The Daily Rx Load Process 401 is described below with respect to FIG. 4:

| | |
|---|---|
| Script Use | Loaddaily.sh is the unix shell script that uses the SQL Loader Rx Control file to convert the Rx Text file from SITE 1 into LOAD_YYYYMMDD, {DNU}_YYYY MMDD Oracle tables after doing all the necessary number, char and date conversions. The {DNU} list contains BLUFFCREEK, KROGER, OMNI, PCN, VIP and WALGREENS. |
| Input | YYYYMMDD.synergy.log.gz, RX Control file, YYYYMMDD.ctl. |
| Output | LOAD_19991123, 24 etc. tables for each day of a month. WALGREENS_YYYYMMDD etc. tables for each DNU company. ../log/YYYYMMDD.log ../data/YYYYMMDD.synergy.log ../bad/YYYYMMDD.synergy.bad ../discard/YYYYMMDD.synergy.discard. |
| Frequency | Daily |
| Run Time | ~4 hours |

1.2 Monthly Mx Load Process 501

Figure 5:
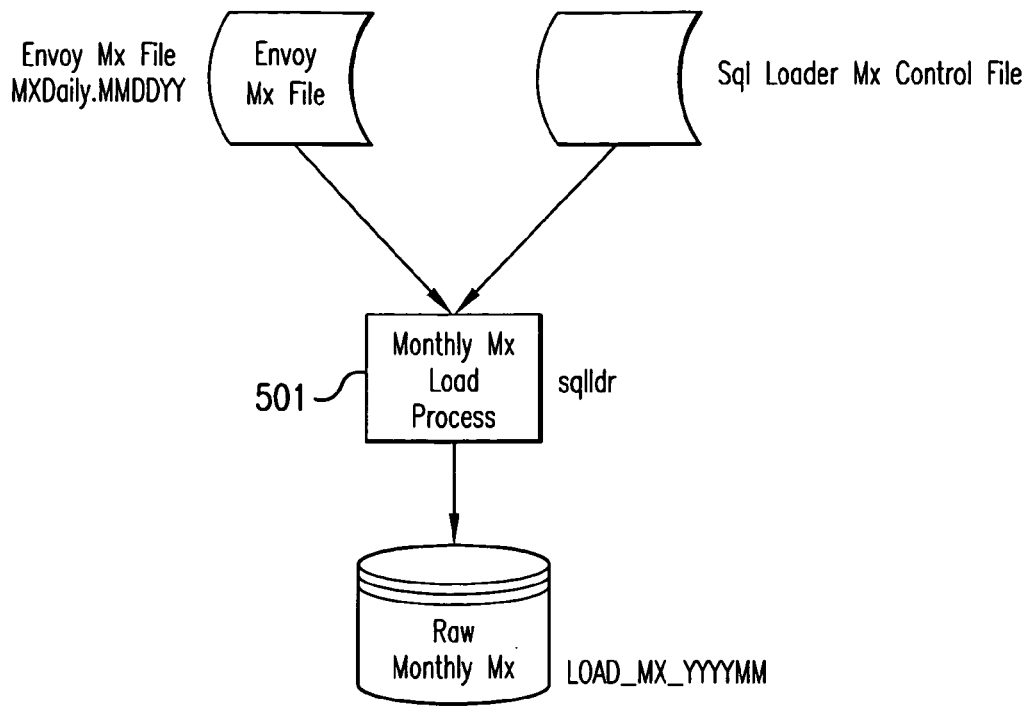
FIG. 5 illustrates the operation of the Monthly Mx Load Process of the present invention.

The Monthly Mx Load Process 501 is described below with respect to FIG. 5:

| | |
|---|---|
| Script Use | SQL LOADER process reads MXDaily.MMDDYY text file and control file to convert it into LOAD_MX_YYYYMM tables. |
| Input | /raid/4011/envoydata/mx/oct1999/data/MXDaily.100199 MX Control file, YYYYMMDD.ctl. |
| Output | LOAD_MX_YYYYMM table. |
| Frequency | Monthly |
| Run Time | ~8 hours |

1.3 Load HX Text Data 601

Figure 6:
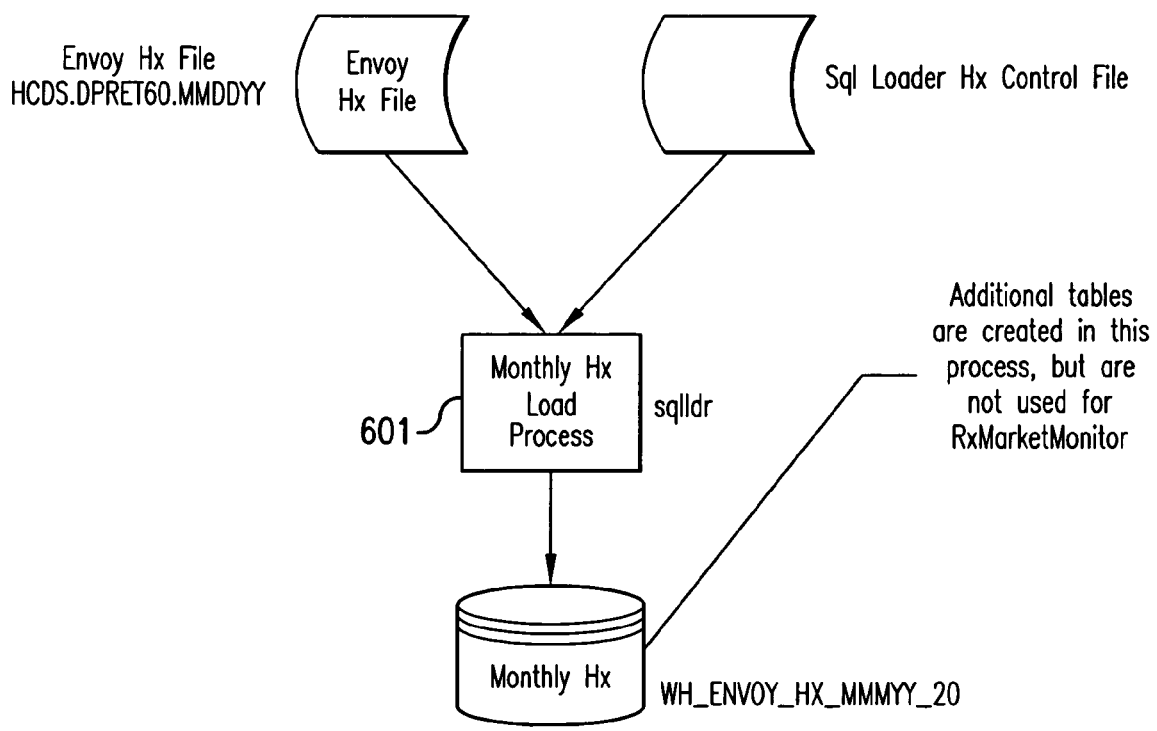
FIG. 6 illustrates the operation of the Monthly Hx Load Process of the present invention.

The Load HX Text Data Process 601 is described below with respect to FIG. 6:

| | |
|---|---|
| Script Use | SQL LOADER process reads HX text file and Control File to convert it into WH_ENVOY_HX_SEP99 tables. |
| Input | /raid/4011/envoydata/hx/sep1999/data/ HCDS.DPRET60.090199, HX Control file, YYYYMMDD.ctl. |
| Output | WH_ENVOY_HX_SEP99_10..20..30..36..40..46..50.. 60..61..66..70..80..90 tables for HX. |
| Frequency | Monthly |
| Run Time | ~8 hours |

1.4 Quarter-Monthly Rx Merge 701

Figure 7:
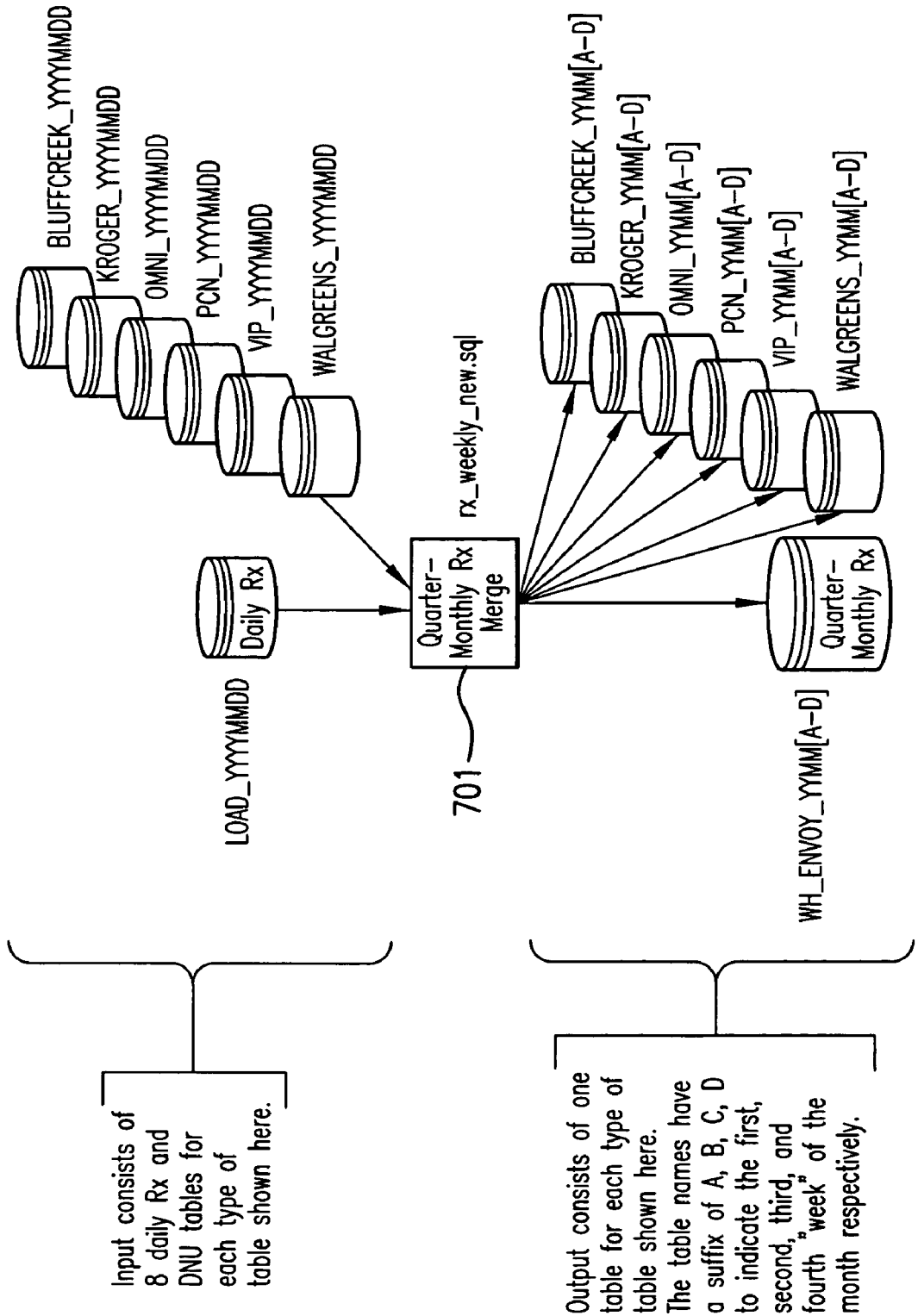
FIG. 7 illustrates the operation of Quarter Monthly Rx Merge Process of the present invention.

The Quarter-Monthly Rx Merge Process 701 is described below with respect to FIG. 7:

| | |
|---|---|
| Script Use | This process uses RX_Weekly_New.sql SQL script to combine all the daily (approx. 8 days of tables) RX and DNU tables into quarter-monthly tables. |
| Input | LOAD_19991123..24 etc. tables for each day of a month. WALGREENS_YYYYMMDD etc. tables for each "DNU" company. |
| Output | WH_ENVOY_9911A..B..C..D etc. 4 tables for a month. WALGREENS_9911A..B..C..D like tables for each "DNU" company for a month. |
| Frequency | Monthly |
| Run Time | ~6 hours |

1.5 Prepare Mx Data (801)

Figure 8:
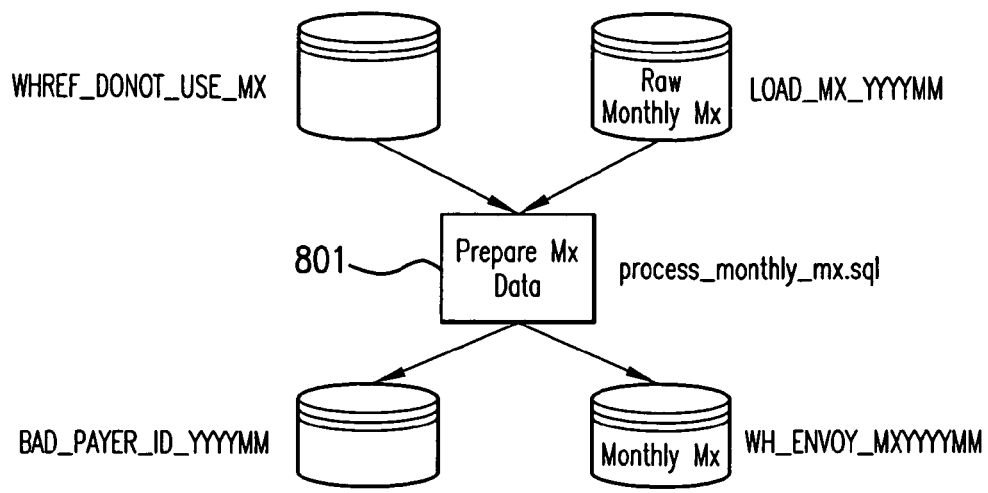
FIG. 8 illustrates the operation of the Prepare Mx Data Process of the present invention.

The Prepare Mx Data Process 801 is described below with respect to FIG. 8:

| | |
|---|---|
| Script Use | This process uses Process_Monthly_MX.sql SQL script to validate and convert LOAD_MX_YYYYMM table data into required date, char and numbers. |
| Input | LOAD_MX_YYYYMM, WHREF_DONOT_USE_MX |
| Output | WH_ENVOY_MX_YYYYMM BAD_PAYER_ID_YYYYMM |
| Frequency | Monthly |
| Run Time | |

2. Produce Patient Data (Step 302)

Figure 9:
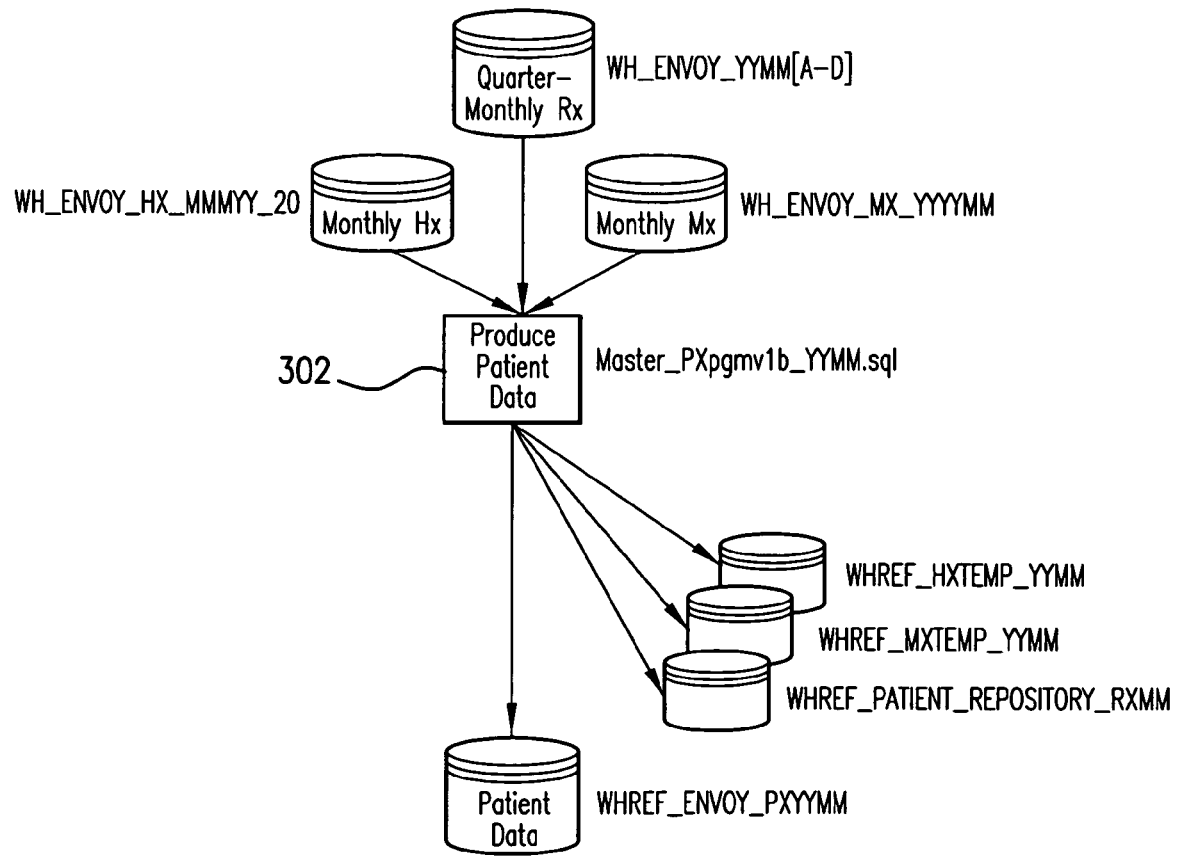
FIG. 9 illustrates the operation of the Produce Patient Data Process of the present invention.

The Produce Patient Data Process of step 302 (FIG. 3) is described below in further detail with respect to FIG. 9:

| | |
|---|---|
| Script Use | This process uses Master_PXpgmv1b_9910.sql SQL script to combine weekly RX and monthly MX, HX tables to create a relational WHREF_ENVOY_PXYYMM table. |
| Input | WH_ENVOY_YYMMA..B etc., WH_ENVOY_MX_YYYYMM, WH_ENVOY_HX_MMMYY_20 tables. |
| Output | WHREF_PATIENT_REPOSITORY_RXMM, WHREF_MXTEMP_YYMM, WHREF_HXTEMP_YYMM, WHREF_ENVOY_PXYYMM tables. |
| Frequency | Monthly |
| Run Time | ~13 hours |

3. Pull Cube Data (Step 303)

Figure 10:
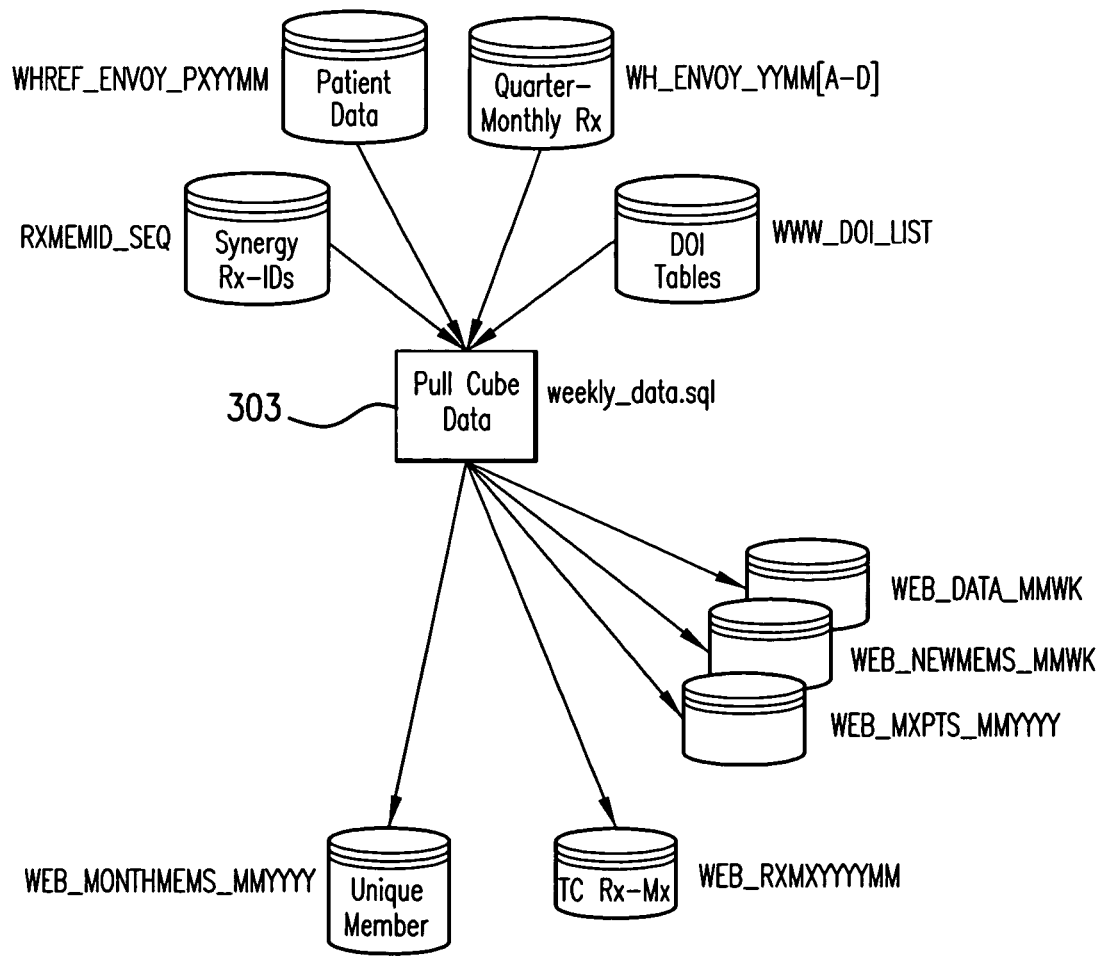
FIG. 10 illustrates the operation of the Pull Cube Data Process of the present invention.

The Produce Patient Data Process of step 303 (FIG. 3) is described below in further detail with respect to FIG. 10:

This process uses a series of Oracle stored procedures to allow for error checking and audit logging. Logging for these procedures uses the MM_LOG table. These stored procedures are called from the Unix shell using shell script wrappers that input the necessary variable values. The stored procedures used are as follows:

```
mm00_init
mm01_set_vars
mm02_weekly_data_pull
mm03_memids
mm04_mx_diags
```

3.1 Audit Logging in Oracle Table MM_LOG

Structure of the MM_LOG table.

| RUN_DATE | START_TIME | STOP_TIME | CUBE_NAME | PROCESS | RETURN_CODE | ERROR_CODE | DESCR |
|---|---|---|---|---|---|---|---|
| 10-Jul-00 | 8:26:37 | 8:26:38 | | mm00_init( ) | 0 | | Completed Procedure mm00_init( ) completed successfully. |
| 10-Jul-00 | 8:26:38 | 8:26:38 | | mm01_set_vars( ) | 0 | | Completed Procedure mm01_set_vars( ) completed successfully. |
| 11-Jul-00 | 8:26:38 | 12:35:49 | | mm02_weekly_data_pull( ) | 0 | | Completed Procedure mm02_weekly_data_pull( ) completed successfully. |
| 11-Jul-00 | 2:04:59 | 12:11:57 | | mm03_memids( ) | 0 | | Completed Procedure mm03_memids( ) completed successfully. |
| 11-Jul-00 | 1:07:32 | 11:23:46 | | mm04_mx_diags( ) | 1 | −904 | ORA-00904: invalid column name |

A record is added to MM_LOG for each process. The name of the process is in the PROCESS column. For cube specific processes, the name of the cube is in the CUBE_NAME column. When a process successfully completes, the RETURN_CODE column contains a 0; when there is an error, the RETURN_CODE column contains a 1.

3.2 Initialization

| | |
|---|---|
| Script Use | The mm00_init procedure initializes the environment for weekly Market Monitory cube processing. The mm00.sh shell script calls the mm00_init procedure. |
| Input | None |
| Output | MM_LOG table truncated. |
| | MM_VARS table truncated. |
| | CUBE_DATA_TEXT table truncated. |
| | MM_LOG table - row inserted showing successful completion or error condition. |

3.3 Set Variables

| | |
|---|---|
| Script Use | The mm01_set_vars procedure sets variables for the Rx Market Monitor weekly cube processing. The mm01.sh shell script calls the mm01_set_vars procedure with input variables set as text. The mm00_init procedure must already have been run. |
| Input | p_run_date Run date of pull as text 'YYYYMMDD'. |
| | p_start_date Start date of pull as text 'YYYYMMDD'. |
| | p_end_date End date of pull as text 'YYYYMMDD'. |
| | p_post_date Post date of pull as text 'YYYYMMDD'. |
| | p_acute_lookback Acute lookback date as text 'YYYYMMDD'. |
| | p_chronic_lookback Chronic lookback date as text 'YYYYMMDD'. |
| Output | MM_VARS table - row inserted with this week's values as DATE datatype. |
| | MM_VARS_HIST table - row inserted with this week's values as DATE datatype. |
| | MM_LOG - row inserted showing successful completion or error condition. |

3.4 Pull Weekly Data

| | |
|---|---|
| Script Use | The mm02_weekly_data_pull procedure pulls one week of Rx data for weekly Rx Market Monitor cube processing. The mm02.sh shell script calls this procedure with the tablespace variable input set. The mm00_init and mm01_set_vars procedures must already have been run. |
| Input | p_tablespace Tablespace name as text. |
| | MM_VARS table |
| | WH_ENVOY_YYMM where YYMM is the two character year and month from start_date in MM_VARS table. |
| | WWW_MASTER_DOI |
| Output | Last week's WEB_DATA_WEEK_PULL table is renamed to WEB_DATA_WEEK_PULL_YYYYMMDD where YYYYMMDD is one day before the start_date in MM_VARS table. |
| | New WEB_DATA_WEEK_PULL table is created in the WEB schema in the tablespace named in the p_tablespace parameter. The WEB_DATA_WEEK_PULL table contains Rx data from the start and end dates in the MM_VARS table. |
| | MM_LOG - a row is inserted to indicate either successful completion or error condition. |

3.5 Get Memids

| | |
|---|---|
| Script Use | The mm03_memids procedure accumulates six weeks of memids. The mm03.sh shell script calls this procedure and inputs the tablespace parameter. The mm00_init, mm01_set_vars, and mm02_weekly_data_pull procedures must already have been run. |
| Input | p_tablespace Tablespace name as text. |
| | MM_VARS table |
| | ALL_MEM_TO_CONVERT table |
| | WEB_DATA_WEEK_PULL_V2 table |
| | WEB_UMEMS_WEEK_V2_MONDD table where MONDD is the end_date from MM_VARS table as text. |
| | WEB_UMEMS_WEEK_V2_MONDD[1-5] tables where MONDD[1-5] are the previous five weeks of data. |
| | RXMEMID_SEQ table |
| Output | WEB_UMEMS_WEEK_V2_MONDD table is created where MONDD is start_date in MM_VARS table minus one day. |
| | WEB_UMEMS_WEEK_PULL is created with data for current week and previous 5 weeks. |
| | MM_LOG - a row is inserted to indicate either successful completion or error condition. |

3.6 Get Mx Diagnoses

| | |
|---|---|
| Script Use | The mm04_mx_diags procedure gets diagnoses information from Mx tables for weekly processing. The mm04.sh shell script executes this procedure with the tablespace input variable set. The mm00_init, mm01_set_vars, mm02_weekly_data_pull, and mm03_memids procedures must already have been run. |
| Input | p_tablespace    Tablespace name as text.<br>MM_VARS table<br>WEB_UMEMS_WEEK_PULL_V2 table<br>MASTER_PX table<br>WEB_MXPTS_WEEK_PULL_V2 table<br>WH_ENVOY_MX_YYYYMM[1-3] tables where YYYYMM[1-3] are the current month and two prior months of data.<br>WEB_RXMX_WEEK_PULL_V2 table<br>RXMEMID_SEQ table |
| Output | ACUTE_RXMX table - records from the week are appended.<br>CHRONIC_RXMX table - records from the week are appended.<br>MM_LOG table - row inserted to indicate either successful completion or error condition. |

4. Generate TC Cube Data (Step 304)

Figure 11:
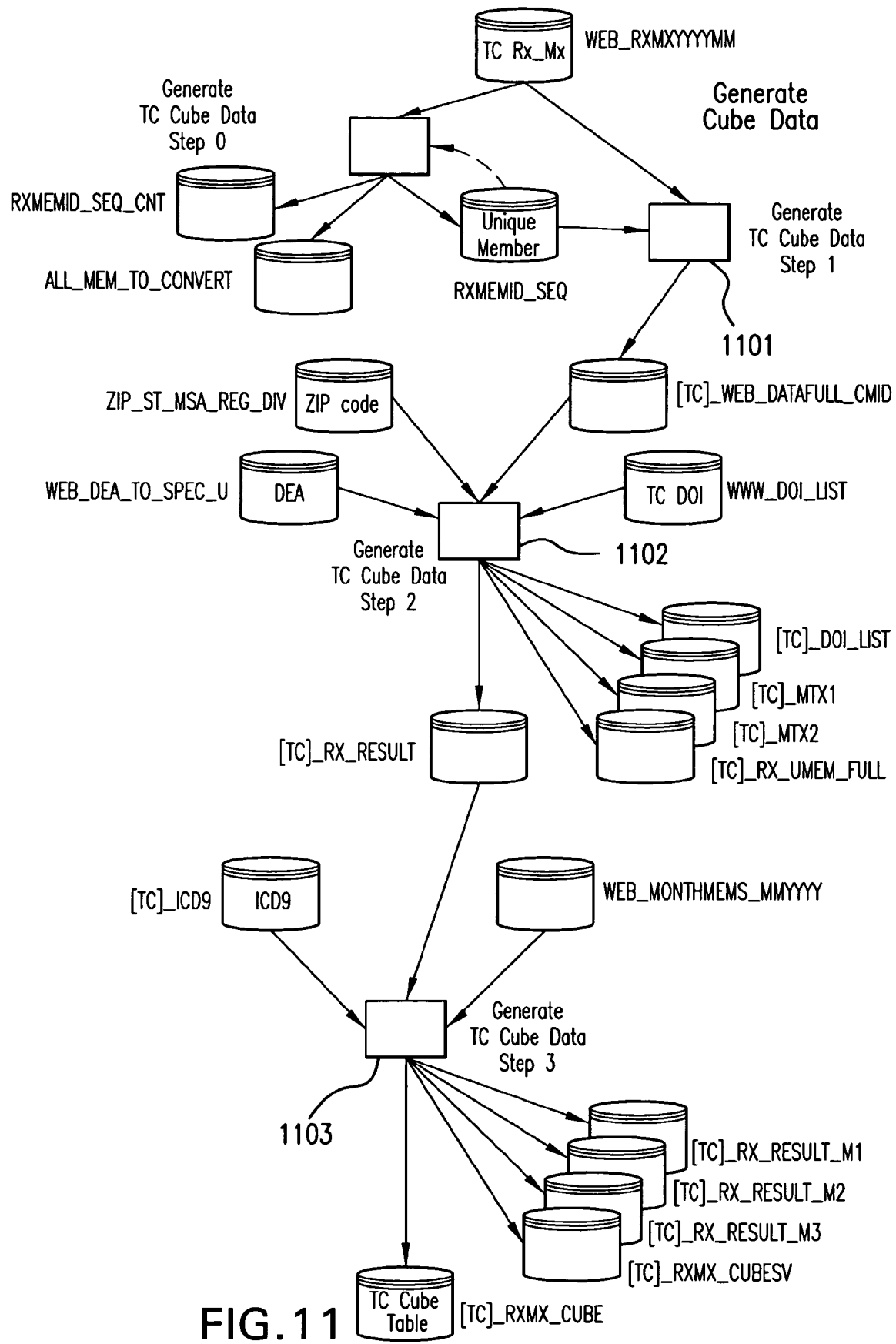
FIG. 11 illustrates the operation of the Generate TC Cube Data Process of the present invention.

The Generate TC Cube Data Process of step 304 (FIG. 3) is described below in further detail with respect to FIG. 11:

The Generate TC Cube Data Process 304 uses three Oracle stored procedures to generate a cube table which will be further used by data transformers to build a COGNOS readable multi-dimensional formatted cube structure. The last stored procedure updates statistics for each cube. The stored procedures are as follows:

> mm05_step1
> mm06_step2
> mm07_step3
> mm08_cube_metadata

4.1 Process Step 1101 (Step 1)

Script Use The mm01_step1 procedure must be run for each therapeutic class. This procedure inserts records into the CMID_V2_CLASS table where CLASS is the p_class specified. The mm00_init, mm01_set_vars, mm02_weekly_data_pull, mm03_memids, and mm04_mx_diags procedures must already have been run.

| | | |
|---|---|---|
| Input | p_class | Class name. |
| | p_tablespace | Tablespace name as text. |
| | p_lookback | Number of days of lookback |
| | p_condition | "ACUTE" or "CHRONIC" |
| | MM_VARS table | |
| | WEB_DATA_WEEK_PULL_V2 table | |
| | CUBE_V2_LIST table | |
| | CMID_V2_CLASS table where CLASS is the p_class. | |
| Output | Records inserted into CMID_V2_CLASS table where CLASS is the p_class.<br>New CMID_V2_CLASS_TMP table is created where CLASS is the p_class.<br>MM_LOG table - row inserted to indicate either successful completion or error condition. | |

4.2 Process Step 1102 (Step 2)

| | |
|---|---|
| Script Use | The mm06_step2 procedure must be run for each therapeutic class. This procedure inserts records into the RX_RESULT_V2_CLASS table where CLASS is the p_class specified when the procedure is called. The mm00_init, mm01_set_vars, mm02_weekly_data_pull, mm03_memids, mm04_mx_diags, and mm05_step1 procedures must already have been run. |
| Input | p_class    Class name.<br>p_tablespace    Tablespace name as text.<br>p_lookback    Number of days of lookback<br>p_condition    "ACUTE" or "CHRONIC"<br>MM_VARS table<br>CMID_V2_CLASS_TMP table where CLASS is the p_class.<br>CMID_V2_CLASS table where CLASS is the p_class.<br>RX_RESULT_TEMP_CLASS table where CLASS is the p_class.<br>ZIP_ST_MSA_REG_DIV table<br>WEB_DEA_TO_SPEC_U |
| Output | New records are inserted into RX_RESULT_V2_CLASS where CLASS is p_class.<br>MM_LOG table - row inserted to indicate either successful completion or error condition. |

4.3 Process Step 1103 (Step 3)

| | |
|---|---|
| Script Use | The mm07_step3 procedure must be run for each therapeutic class. This procedure creates a new RXMX_CUBE_V2_CLASS table where class is the p_class specified. The mm00_init, mm01_set_vars, mm02_weekly_data_pull, mm03_memids, mm04_mx_diags, mm05_step1, and mm06_step2 procedures must already have been run. |
| Input | p_class    Class name.<br>p_tablespace    Tablespace name as text.<br>p_lookback    Number of days of lookback<br>p_condition    "ACUTE" or "CHRONIC"<br>RXMX_CONDITION_V2 table where CONDITION is the p_condition.<br>RX_RESULT_V2_CLASS table where CLASS is the p_class.<br>ICD9_V2_CLASS table where CLASS is the p_class.<br>RX_RESULT_V2_CLASS_M table where CLASS is the p_class. |
| Output | New RXMX_CUBE_V2_CLASS table is created where CLASS is p_class.<br>MM_LOG table - row inserted to indicate either successful completion or error condition. |

4.4 Generate Cube Metadata

| | |
|---|---|
| Script Use | The mm08_cube_metadata procedure must be run for each therapeutic class. This procedure updates the CUBE_DATA table for each cube. The mm00_init, mm01_set_vars, mm02_weekly_data_pull, mm03_memids, mm04_mx_diags, mm05_step1, mm06_step2 and mm07_step3 procedures must already have been run. |

-continued

| | |
|---|---|
| Input | p_class    Class name.<br>MM_VARS table<br>CUBE_DATA table where<br>CLASS is the p_class. |
| Output | CUBE_DATA_TEXT table<br>is appended where CLASS is p_class.<br>MM_LOG table - row inserted to indicate<br>either successful completion<br>or error condition. |

5. Build Cube (Step 305)

Figure 9A:
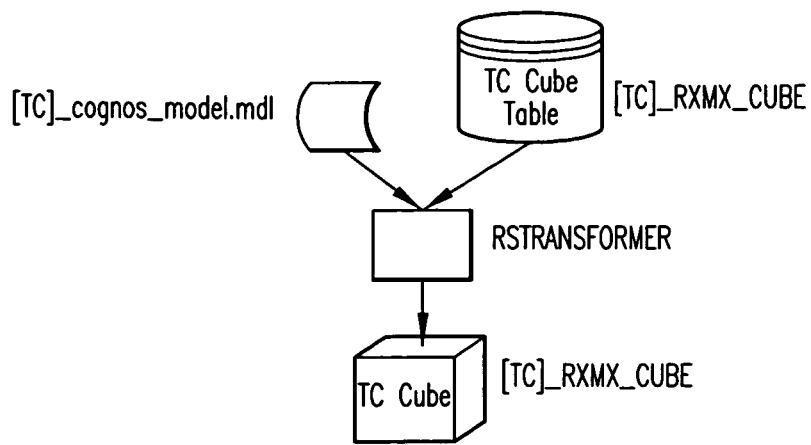
FIG. 9A illustrates the operation of the RSTRANSFORMER process of the present invention.

The Build Cube Process of step 305 (FIG. 3) is described below in further detail with respect to FIG. 9A:

This process uses a C program to create a cube for each therapeutic class. Each cube is FTP'd to the server of SITE 3. Metadata for each cube is spooled to a text file and FTP'd to the SITE 3 server. The same text files may be concatenated and sent via email to the web developer of SITE 2.

5.1 Build Cube

| | |
|---|---|
| Script Use | The program RSSERVER is repeated<br>for each of the therapeutic classes<br>and called by the script mmv2_'class<br>name'.sh. Data Transformers uses<br>Model Structure and OBES_RX_CUBE<br>Oracle table (built in above<br>process) to finally build a CUBE for<br>each of the therapeutic class. This<br>Cube is then used by COGNOS to<br>show requested information on the<br>Web. |
| Input | OBES_RXMX_CUBE |
| Output | Cube for a OBES Class |
| Frequency | On Request |
| Run Time | ~8 hours |

5.2 FTP Cube to SITE 3 Server

| | |
|---|---|
| Script Use | The transfer_mm_cube.sh script<br>renames a cube and puts a copy into<br>directory /raid4011/cubes/transfer where it will<br>automatically be FTP'd to the SITE 3 server.<br>This script is run in parallel for each class<br>(class corresponds to cube). |

5.3 Approve Cube

| | |
|---|---|
| Script Use | The approve_cube script is run<br>manually for each cube after quality<br>assurance has been performed. This script is<br>run in parallel for each<br>class (class responds to cube). |

5.4 Create Metadata Text File/FTP to SITE 3 Server

| | |
|---|---|
| Script Use | The process gen_mm_file.sql is called<br>by gen_mm_file.sh to spool<br>metadata for a cube to a text file.<br>The text file is put into a directory<br>where it is automatically FTP'd to<br>the SITE 3 server. This script is run<br>in parallel for each class. All procedures<br>to pull cube data must have |

-continued

| | |
|---|---|
| | been successfully completed and<br>the metadata must exist in the Oracle<br>tables cube_data and<br>cube_data_text. |

5.5 E-mail Metadata to Web Developer

| | |
|---|---|
| Script Use | The email_meta.sh script will<br>e-mail metadata to a SITE 2 Web<br>Developer. This script is run in parallel<br>for each class (class<br>corresponds to cube). |

6. Automated Cube Deployment and MetaData Update Process

Automated processes exist on the OnLine Analytical Processing (OLAP) host machine to deploy data cubes (such as QUINTERNET™ Series, from Quintiles Transnational Corp.) to the production web site, cubes ready for Quality Assurance (QA) verification, as well as to automatically update "metadata" on production web pages. This enables production cube deployments and web page updates to occur during off-peak hours without any manual intervention.

As a QUINTERNET™ Series data cube is created, the cube is sent via a secure connection to the host machine. The cube is then automatically "served up" to the QA location on the web, to which only authorized personnel have access.

For each cube approval, a "metadata" file is transmitted from the SITE 2 server, via a secure connection, to the host machine in a specific location (directory within a file system). This secure transmission may occur after a data cube has passed the QA verification.

The metadata file contains statistical information about the specific cube (e.g.—date that cube contains data through, number of records, number of patients, etc.). Several times each night, an automated process may be initiated which checks for the presence of a metadata file and a corresponding data cube file. If matching files for a specific cube exist, the process automatically "serves" up this cube into production for access via the web pages. In addition, the HTML page which contains the metadata for the cube is updated with the metadata contained in the metadata file.

The server at, for example, SITE 3 may prepare and maintain HTML template files for each QUINTERNET™ Series cube. These files contain the base HTML used to create each cube's web page. Instead of the actual metadata values that will populate the cubes' web pages, the HTML template files may contain placeholder tags. These placeholder tags are replaced by data values supplied by SITE 2 in metadata files.

SITE 2 transfers the template files and the metadata files to a host via FTP. The metadata files are transferred to the host each time a cube is approved. Template files are maintained for each QUINTERNET™ Series cube and are updated by SITE 2 as necessary so that a current version of each cube's template file is always available for processing on the host.

After a cube has been updated, reviewed for quality and approved by the operator of SITE 2, SITE 2 transfers a metadata file for that cube to the host via FTP. The metadata files contains the same tags found in the HTML template file for each cube. Each of these tags is coupled with a value that will be substituted for the placeholder tag in the HTML template file.

An event-driven file processing script runs periodically via cron, a unix scheduling system, on the host. If the file processing script detects the existence of a designated flag file, a script called enable_cube.ksh is run. The enable_cube.ksh script calls a Perl script, replaceHtmlMetaTags.pl, passing it the name of the cube being processed and the name of the related metadata file. The enable_cube.ksh script also updates the metadata file with a tag/value pair representing the date the updated cube is being deployed.

Figure 1C:
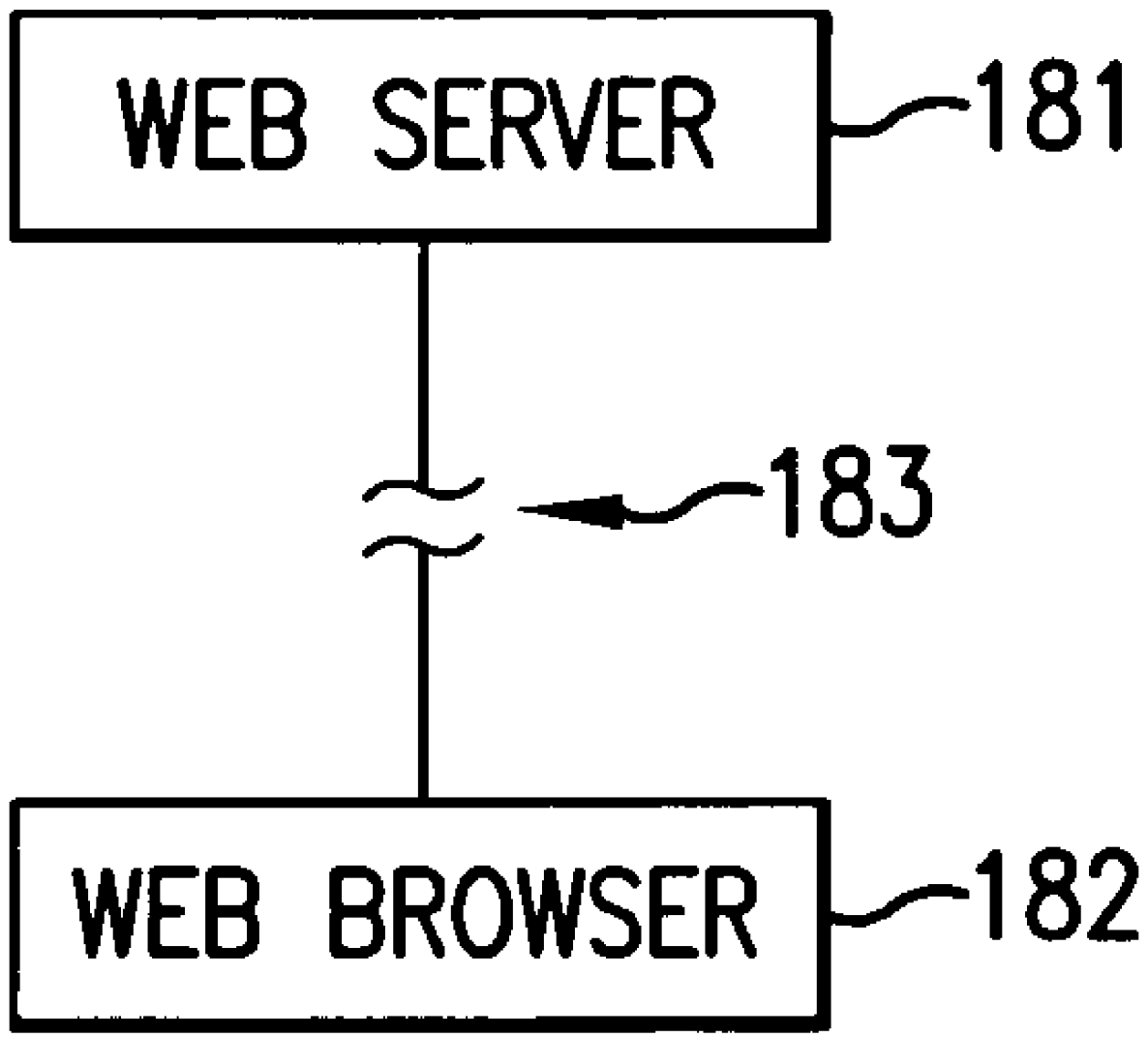
Figure 2A:
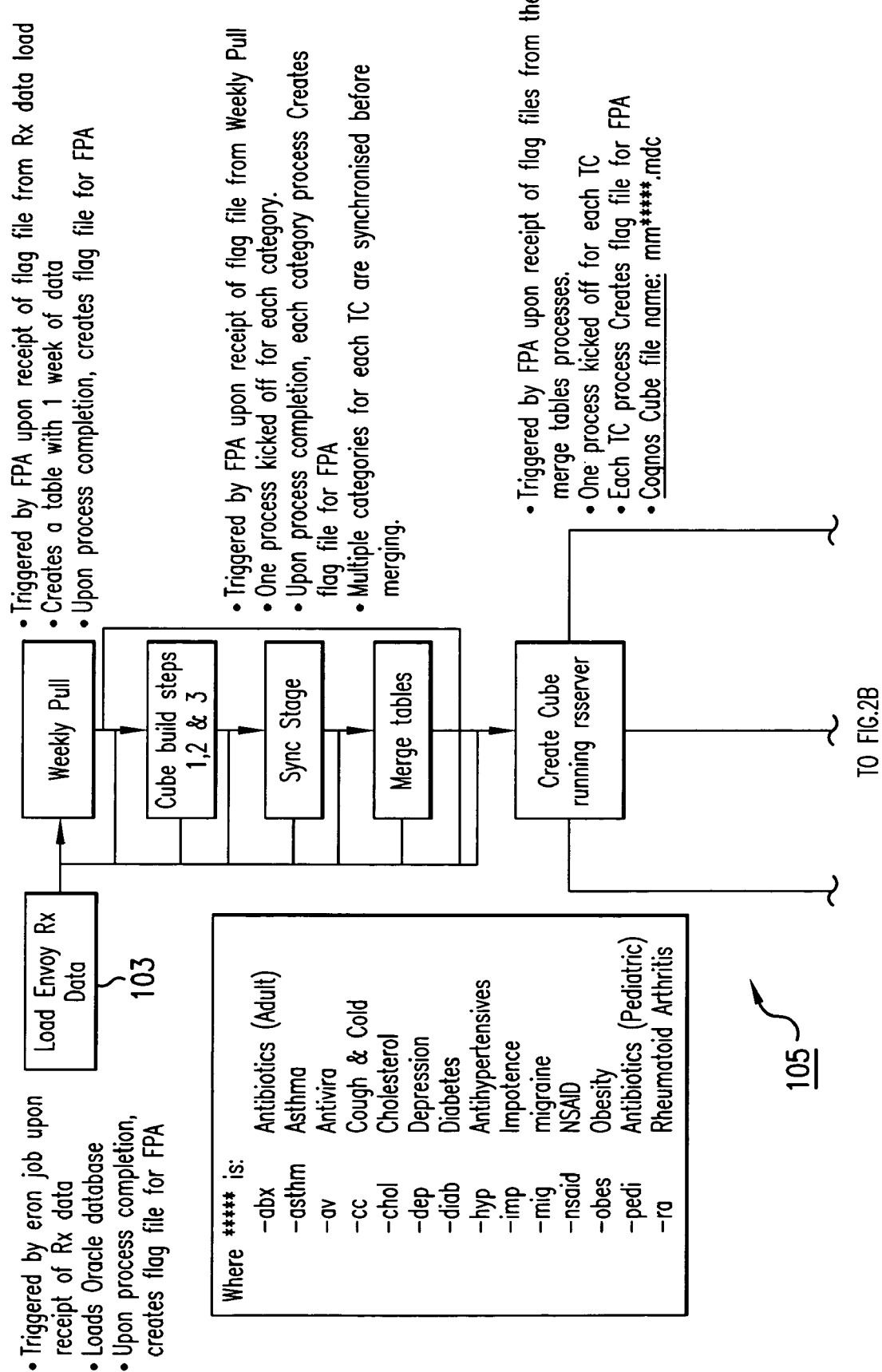
Figure 2B:
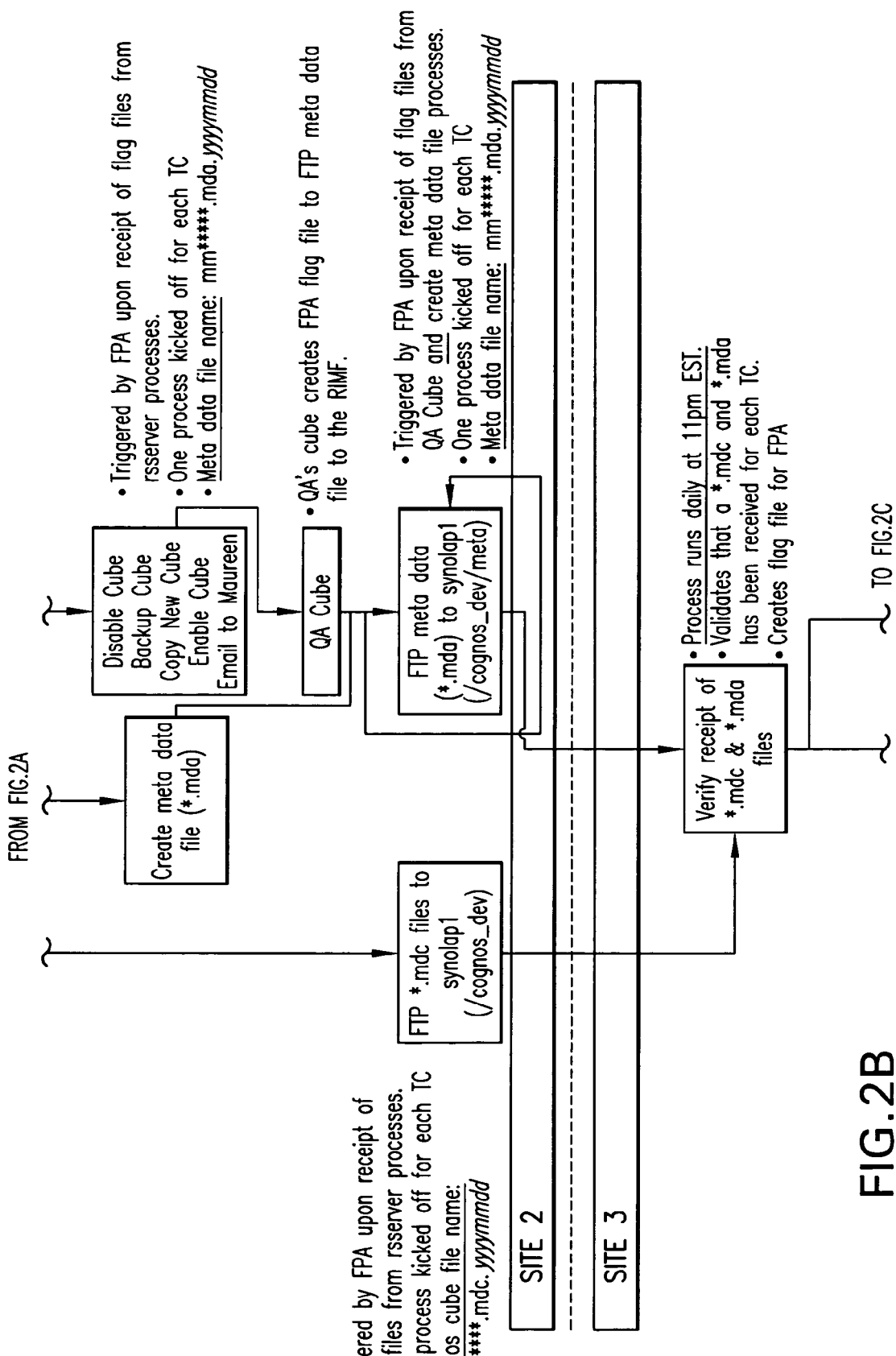

The purpose of the replaceHtmlMetaTags.pl script is to automatically generate HTML pages for the QUINTERNET™ Series products. The replaceHtmlMetaTags.pl script substitutes the values in the metadata file for the placeholder tags in the template and saves the resulting output in an HTML file. Referring to FIG. 1C, the enable_cube.ksh script then promotes the updated HTML file(s) to SITE 3's web server 181 thus making it available via, for example, the Internet 183, to users of web browsers 182 operating on client computers.

The present invention may be implemented with a processing schedule defined in many ways. For example, the schedule may be on a weekly or monthly basis, depending upon the needs of the implementation. At times, special requests may be required and the ability to process data and create cubes on an ad hoc basis exists.

While there has been shown the preferred embodiment of the present invention, it is to be understood that certain changes can be made in the forms and arrangements of the elements of the system and the steps of the method without departing from the spirit and scope of the invention as is set forth in the claims.

The invention claimed is:

1. A method for creating a unique alias associated with an individual identified in at least a first health care database, wherein the first health care database contains at least one record comprising a plurality of identification fields and a health care field that comprises health care data associated with the individual, the method comprising:
  (a) selecting a first record within the first health care database, wherein the first record comprises a first plurality of identification fields and a first health care field that comprises health care data associated with the individual;
  (b) selecting a first subset of the first plurality of identification fields within the first record;
  (c) creating a first concatenated identifier using the selected first subset of identification fields;
  (d) defining a first unique alias by encrypting at least a part of the first concatenated identifier; and
  (e) transmitting the first unique alias and the first health care field to a data store that stores the first unique alias and the first health care field.

2. The method of claim 1, wherein the selected first subset comprises at least last name, birthday, and gender.

3. The method of claim 1, wherein health care data comprises at least one of pharmaceutical claims data, medical claims data, or hospital claims data.

4. The method of claim 1, further comprising:
  (a) receiving the first alias and the first health care field; and
  (b) storing the first alias and the first health care field in the data store.

5. The method of claim 4, further comprising creating a linked plurality of health care fields by linking the first health care field with at least one health care field from one or more other records using the first unique alias.

6. The method of claim 5, further comprising performing market analysis using the linked plurality of health care fields.

7. The method of claim 5, further comprising performing pharmaceutical analysis using the linked plurality of health care fields.

8. The method of claim 5, further comprising performing medical condition analysis using the linked plurality of health care fields.

9. The method of claim 5, further comprising performing patient analysis using the linked plurality of health care fields.

10. The method of claim 5, further comprising:
  (a) receiving a second unique alias and a second health care field, wherein the second unique alias comprises an encrypted concatenated subset of identification fields from a health care record associated with the individual; and
  (b) storing the second unique alias and the second health care field in the data store.

11. The method of claim 10, further comprising linking the first health care field with the second health care field using the first unique alias and the second unique alias.

12. The method of claim 1, further comprising:
  (a) selecting a second record within a second health care database, wherein the second record comprises a second plurality of identification fields and a second health care field that comprises health care data associated with the individual;
  (b) selecting a second subset of the second plurality of identification fields within the second record;
  (c) creating a second concatenated identifier using the selected second subset of identification fields;
  (d) defining a second unique alias by encrypting at least a portion of the second concatenated identifier; and
  (e) transmitting the second unique alias and the second health care field to the data store, wherein the data store stores the second unique alias and the second health care field.

13. The method of claim 12, further comprising:
  (a) receiving the first unique alias and the first health care field;
  (b) storing the first unique alias and the first health care field in the data store;
  (c) receiving the second unique alias and the second health care field; and
  (d) storing the second unique alias and the second health care field in the data store.

14. The method of claim 13, further comprising creating a linked first and second health care field by linking the first health care field with the second health care field using the first unique alias and the second unique alias.

15. The method of claim 14, further comprising performing market analysis using the linked first and second health care field.

16. The method of claim 14, further comprising performing pharmaceutical analysis using the linked first and second health care field.

17. The method of claim 14, further comprising performing medical condition analysis using the linked first and second health care field.

18. The method of claim 14, further comprising performing patient analysis using the linked first and second health care field.

19. A method for creating a unique alias associated with an individual identified in at least a first health care database, wherein the first health care database contains at least one record comprising a plurality of identification fields and a health care field that comprises health care data associated with the individual, the method comprising:
(a) selecting a first record within the first health care database, wherein the first record comprises a first plurality of identification fields and a first health care field that comprises health care data associated with the individual;
(b) selecting a first subset of the first plurality of identification fields within the first record;
(c) creating a first concatenated identifier using the selected first subset of identification fields;
(d) defining a first unique alias by encrypting at least a part of the first concatenated identifier; and
(e) linking the first health care field with a plurality of health care fields taken from one or more other records using the first unique alias.

20. A method for using a unique alias associated with an individual identified in health care databases, wherein each health care database contains at least one record that comprises a plurality of identification fields and a health care field that comprises health care data associated with the individual, the method comprising:
(a) receiving a first unique alias and a first health care field, wherein the first unique alias was created by performing the steps of:
  i. selecting a first record within a first health care database, wherein the first record comprises a first plurality of identification fields and a first health care field that comprises health care data associated with the individual;
  ii. selecting a first subset of the first plurality of identification fields within the first record;
  iii. creating a first concatenated identifier using the selected first subset of identification fields; and
  iv. creating the first unique alias by encrypting at least a part of the first concatenated identifier;
(b) receiving a second unique alias and a second health care field, wherein the second unique alias was created by performing the steps of:
  i. selecting a second record within a second health care database, wherein the second record comprises a second plurality of identification fields and a second health care field that comprises health care data associated with the individual;
  ii. selecting a second subset of the second plurality of identification fields within the second record;
  iii. creating a second concatenated identifier using the selected second subset of identification fields; and
  iv. creating the second unique alias by encrypting at least a part of the second concatenated identifier;
(c) linking the first health care field with the second health care field using the first unique alias and the second unique alias; and
(d) performing health care data analysis using the linked first and second health care fields.

* * * * *